United States Patent
Schaal et al.

(10) Patent No.: US 11,727,561 B2
(45) Date of Patent: *Aug. 15, 2023

(54) AUTOMATED METHODS FOR THE OBJECTIVE QUANTIFICATION OF RETINAL CHARACTERISTICS BY RETINAL REGION AND DIAGNOSIS OF RETINAL PATHOLOGY

(71) Applicant: UNIVERSITY OF LOUISVILLE RESEARCH FOUNDATION, INC., Louisville, KY (US)

(72) Inventors: Shlomit Schaal, Prospect, KY (US); Ayman El-Baz, Louisville, KY (US); Amir Reza Hajrasouliha, Chicago, IL (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 240 days.

This patent is subject to a terminal disclaimer.

(21) Appl. No.: 17/138,222

(22) Filed: Dec. 30, 2020

(65) Prior Publication Data
US 2021/0125336 A1    Apr. 29, 2021

Related U.S. Application Data

(63) Continuation of application No. 15/776,385, filed as application No. PCT/US2016/020280 on Mar. 1, 2016, now Pat. No. 10,891,729.
(Continued)

(51) Int. Cl.
*G06V 10/00* (2022.01)
*G06T 7/00* (2017.01)
(Continued)

(52) U.S. Cl.
CPC ............ *G06T 7/0012* (2013.01); *A61B 3/102* (2013.01); *G06T 7/12* (2017.01); *G06T 7/143* (2017.01);
(Continued)

(58) Field of Classification Search
CPC ......... G06T 7/0012; G06T 7/143; G06T 7/12; G06T 7/168; G06T 7/149;
(Continued)

(56) References Cited

U.S. PATENT DOCUMENTS 8,908,189 B2 * 12/2014 Tumlinson ............ H01S 3/0823
                                                     356/497
9,115,974 B2 * 8/2015 Kang ..................... A61B 34/75
(Continued)

OTHER PUBLICATIONS

Supplementary Partial European Search Report, EU Application No. EP 16 86 6774, dated Nov. 19, 2018.
(Continued)

*Primary Examiner* — Amir Alavi
(74) *Attorney, Agent, or Firm* — Dentons Bingham Greenebaum LLP; Brian W. Chellgren

(57) ABSTRACT

Automated and objective methods for quantifying a retinal characteristic include segmenting an optical coherence tomography retinal image into a plurality of layered retinal regions, and quantifying the retinal characteristic for each region as normalized to a range defined by the characteristic value in the vitreous region and in the retinal pigment epithelium region. Such methods are useful for detecting occult ocular pathology, diagnosing ocular pathology, reducing age-bias in OCT image analysis, and monitoring efficacy ocular/retinal disease therapies.

25 Claims, 15 Drawing Sheets

Related U.S. Application Data

(60) Provisional application No. 62/256,980, filed on Nov. 18, 2015.

(51) Int. Cl.
| | |
|---|---|
| *G06T 7/12* | (2017.01) |
| *G06T 7/143* | (2017.01) |
| *G06T 7/168* | (2017.01) |
| *A61B 3/10* | (2006.01) |
| *G06T 7/149* | (2017.01) |

(52) U.S. Cl.
CPC .............. *G06T 7/149* (2017.01); *G06T 7/168* (2017.01); *G06T 2207/10101* (2013.01); *G06T 2207/20064* (2013.01); *G06T 2207/20121* (2013.01); *G06T 2207/20124* (2013.01); *G06T 2207/30041* (2013.01)

(58) Field of Classification Search
CPC . G06T 2207/30041; G06T 2207/20124; G06T 2207/20121; G06T 2207/10101; G06T 2207/20064; A61B 3/102
See application file for complete search history.

(56) References Cited

U.S. PATENT DOCUMENTS

| | | | | |
|---|---|---|---|---|
| 9,164,240 | B2* | 10/2015 | Schmitt | G01B 9/02091 |
| 9,400,169 | B2* | 7/2016 | Zhou | A61B 5/0066 |
| 9,404,800 | B2* | 8/2016 | Wong | A61B 5/7225 |
| 9,636,011 | B2* | 5/2017 | Sharma | G01J 3/2823 |
| 10,062,162 | B2* | 8/2018 | Lowry | G06T 7/11 |
| 10,231,619 | B2* | 3/2019 | Huang | A61B 3/0025 |
| 10,463,247 | B2* | 11/2019 | Chen | A61B 3/102 |
| 10,849,789 | B2* | 12/2020 | Dewey | A61B 3/107 |
| 10,891,729 | B2* | 1/2021 | Schaal | G06T 7/143 |
| 11,099,000 | B2* | 8/2021 | Mohseni | A61B 5/0066 |
| 2012/0150029 | A1 | 6/2012 | Debuc | |
| 2013/0294009 | A1 | 11/2013 | Takeuchi et al. | |

OTHER PUBLICATIONS

Andrew Lang et al.: "Retinal layer segmentation of macular OCT images using boundary classification", Biomedical Optics Express, vol. 4, No. 7, Jun. 14, 2013, p. 1133, XP055531993, United States.

Gilem'Farb G et al: "Expectation-maximization for a linear combination of Gaussians", Pattern Recognition, 2004, ICPR 2004, Proceedings of The 17th International Conference on Cambridge, UK Aug. 23-26, 2004, Piscataway, NJ vol. 3, Aug. 23, 2004, pp. 422-425, XP010724688.

Ayman El-Baz et al.: "Precise Segmenation of 3-D Magnetic Resonance Angography", IEEE Transactions on Biomedical Engineering, IEEE Service Center, Piscataway, NJ, USA vol. 59, No. 7, Jul. 1, 2012, pp. 2019-2029, XP011490131.

* cited by examiner

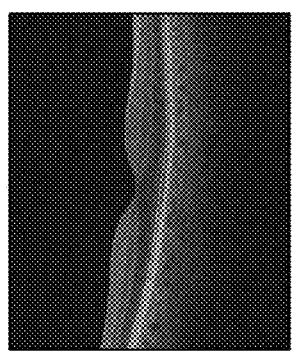
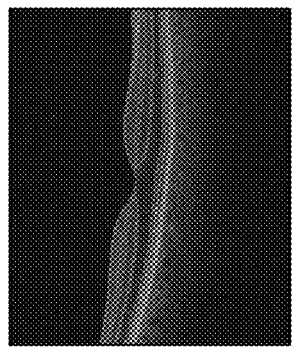
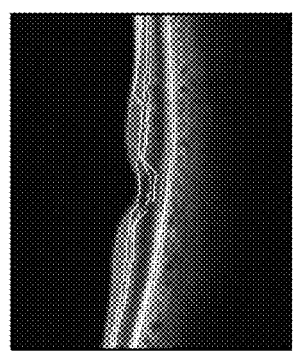
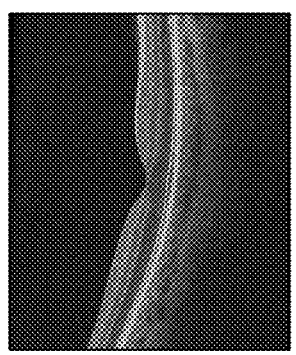
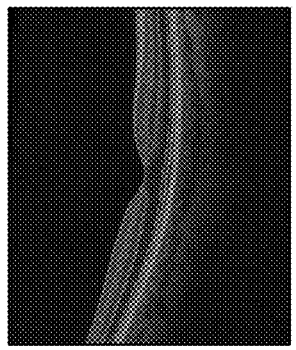
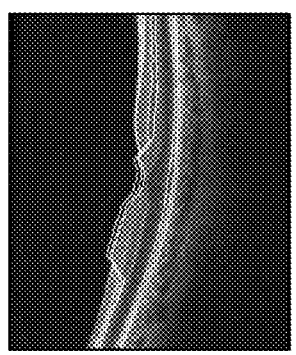
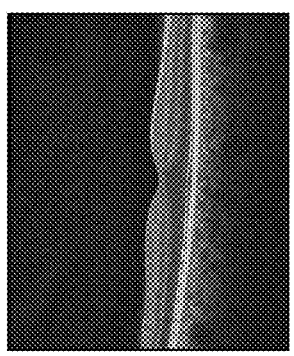
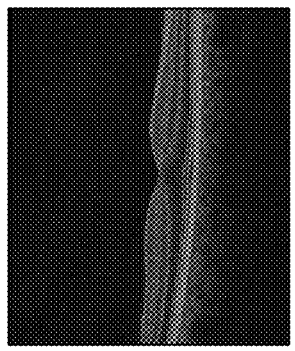
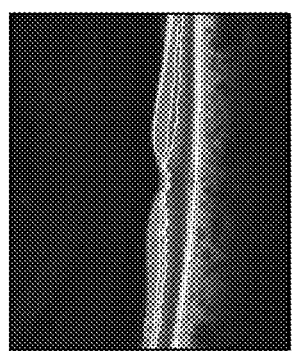
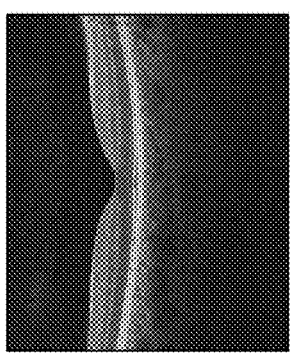
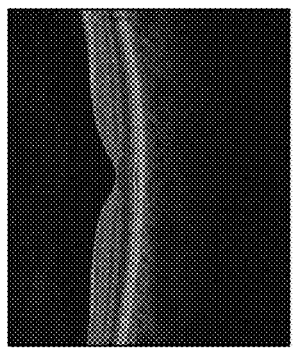
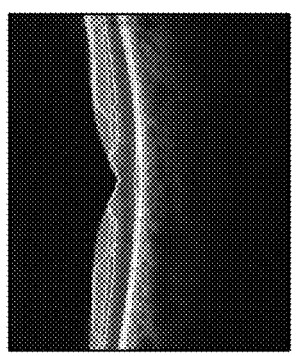
FIG. 5A
FIG. 5B
FIG. 5C

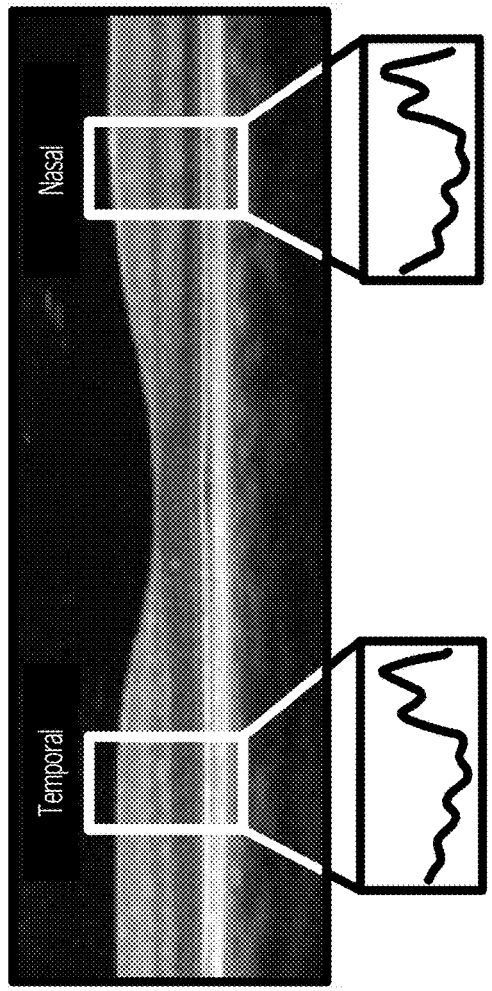
FIG. 6A
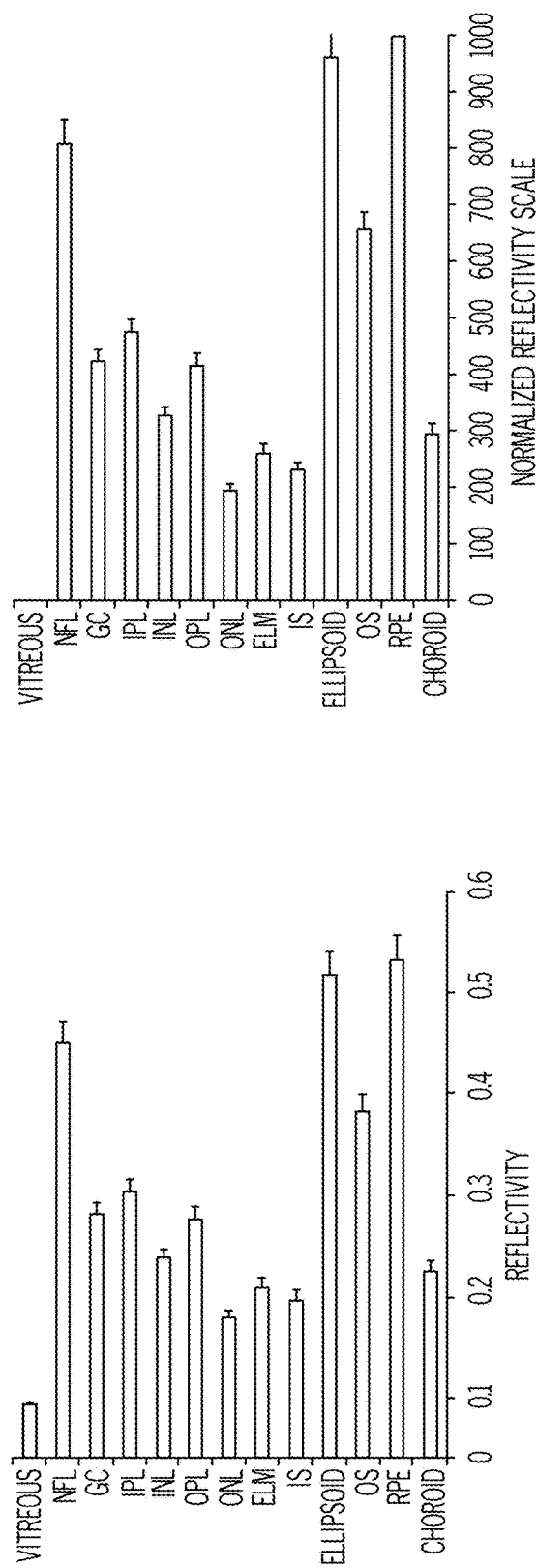
FIG. 6B
FIG. 6C

| AGE GROUPS | 10-19 | 20-29 | 30-39 | 40-39 | 50-59 | 60-69 | 70-79 | 80-89 | 90-99 |
|---|---|---|---|---|---|---|---|---|---|
| MEAN AGE, Y | 15.5±2.7 | 23.7±3.5 | 33.4±3.1 | 45.6±2.5 | 55.0±3.1 | 65.3±2.8 | 74.6±2.8 | 84.3±3.1 | 91.62±2.32 |
| EYES, n | 17 | 22 | 32 | 36 | 50 | 55 | 62 | 39 | 10 |
| MALES, % | 44 | 45 | 53 | 44 | 48 | 45 | 42 | 42 | 60 |
| FEMALES, % | 56 | 55 | 47 | 56 | 52 | 55 | 58 | 58 | 40 |
| CAUCASIANS, % | 100 | 72 | 82 | 82 | 85 | 85 | 90 | 90 | 89 |
| ASIAN, % | 0 | 0 | 0 | 6 | 0 | 0 | 0 | 0 | 0 |
| AFRICAN AMERICANS, % | 0 | 9 | 7 | 12 | 15 | 15 | 10 | 10 | 11 |
| HISPANICS, % | 0 | 19 | 7 | 0 | 0 | 0 | 0 | 0 | 0 |

FIG. 9

AUTOMATED METHODS FOR THE OBJECTIVE QUANTIFICATION OF RETINAL CHARACTERISTICS BY RETINAL REGION AND DIAGNOSIS OF RETINAL PATHOLOGY

CLAIM OF PRIORITY

This application claims priority to U.S. application Ser. No. 15/776,385 filed on May 15, 2018, which claims priority to Application PCT/US2016/020280 filed on Mar. 1, 2016, which claims priority to U.S. Provisional Application No. 62/256,980 filed on Nov. 18, 2015, each of which is incorporated herein by reference.

TECHNICAL FIELD

The present disclosure relates to the field of clinical diagnosis and monitoring of ocular pathologies utilizing spectral domain optical coherence tomography (SD-OCT). Specifically, the disclosure relates to automated methods for segmenting and analyzing an OCT image and automated methods for diagnosing ocular pathology based thereon.

BACKGROUND ART

Spectral domain optical coherence tomography (SD-OCT) is a widely used tool for the diagnosis and evaluation of retinal diseases. Utilizing interferometry, low coherence light is reflected from retinal tissue to produce a two-dimensional grayscale image of the retinal layers. Differences in reflectivity of retinal layers produce different intensities on an SD-OCT scan, allowing for noninvasive visualization of distinct retinal layers. This detailed cross-sectional anatomy of the retina is often referred to as "in-vivo histology" and is instrumental in the assessment of several common retinal pathologies, including diabetic retinopathy (DR), age-related macular degeneration (AMD), macular hole, macular edema, vitreo-macular traction (VMT), choroidal neovascularization, and epiretinal membrane. SD-OCT can be also used to assess retinal nerve fiber layer (RNFL) thickness for the evaluation of glaucoma. Retinal layer morphology and retinal thickness measurements are used to identify and measure retinal abnormalities such as macular edema, and these measurements are also used to monitor disease progression and response to treatment.

However, with the exception of retinal thickness measurements, conventional methods relying on visual inspection of SD-OCT provides limited objective quantitative data, and therefore images must be subjectively interpreted by an eye specialist. As a result, interpretation of SD-OCT is susceptible to human bias and error.

Further, although it is well established that with normal aging of the retina there are a variety of neurochemical, cellular, and molecular changes that occur. Normal aging is also associated with a number of functional changes that seem to occur in the absence of any obvious eye disease. The current techniques for observing and analyzing the aging retina in vivo, including longitudinal OCT imaging in high-risk populations, fail to fully capture the subtle changes that occur such that even with monitoring, disease is not typically diagnosed until irreversible damage has occurred.

The basic SD-OCT image is a histology-equivalent optic reflectivity B-scan retinal section. To-date, however all SD-OCT images are manually interpreted by an ophthalmologist on the basis of anatomic appearance and human pattern recognition. The need for a valid and reliable automated processing method and an un-biased interpretation of retinal scans is pertinent. Accurate reproducible automated SD-OCT image analysis will enable earlier identification of retinal conditions, enable better follow up strategies and plans, eliminate human errors, and allow more efficient and cost-effective patient care. Although initial preliminary automated image processing exists in some commercially available SD-OCT models, it is currently limited to retinal thickness, retinal volume and partial retinal segmentation.

Automated segmentation of retinal layers from SD-OCT images has been previously attempted by several groups. Ishikawa (*Invest Ophthalmol Vis Sci* 2005; 46:2012-2017) developed an automated algorithm that identifies four retinal layers using an adaptive thresholding technique. This algorithm failed with poor-quality images and also failed with some good-quality ones. Bagci (*Am J Ophthalmol.* 2008; 146:679-687) proposed an automated algorithm that extracted seven retinal layers using a customized filter for edge enhancement in order to overcome uneven tissue reflectivity. However, further work is needed to apply this algorithm to more advanced retinal abnormalities. Mishra (*Opt Express.* 2009; 17:23719-23728) applied an optimization scheme to identify seven retinal layers. The algorithm, however, could not separate highly reflective image features. Another automated approach was proposed by Rossant (*IEEE Int Symp Biomed Imag.* 2009; 6:1370-1373) for segmenting eight retinal layers using active contours, k-means, and random Markov fields. This method performed well even when retinal blood vessels shaded the layers, but failed in blurry images. Kajic (*Opt Express* 2010; 18:14730-14744) developed an automated approach to segment 8 layers using a large number of manually segmented images that were used as input to a statistical model. Supervised learning was performed by applying knowledge of the expected shapes of structures, their spatial relationships, and their textural appearances. Yang (*Opt Express.* 2010; 18:21293-21307) devised an approach to segment eight retinal layers using gradient information in dual scales, utilizing local and complementary global gradient information simultaneously. This algorithm showed promise in segmenting both healthy and diseased scans; however has not demonstrated reliable evaluation on retinas affected with outer/inner retinal diseases. Yazdanpanah (*IEEE Trans Med Imag.* 2011; 30:484-496) presented a semi-automated approach to extract 9 layers from OCT images using Chan-Vese's energy-minimizing active contour without edges model. This algorithm incorporated a shape model based on expert anatomical knowledge of retinal layers. The proposed method required user initialization and was never tested on either human retinas or on diseased retinas. Ehnes (*Transl Vis Sci Technol.* 2014; 3:1) developed a graph-based algorithm for retinal segmentation which could segment up to eleven layers in images of different devices. However, the algorithm worked only with high-contrast images. Kafieh (*Medical image analysis.* 2013:17(8): 907-928) also used graph-based diffusion maps to segment the intraretinal layers in OCT scans from normal controls and glaucoma patients. Chui (*Optics express.* 2010:18(18): 19413-19428) proposed an automated approach for segmenting 8 retinal layers using graph theory along with dynamic programming which reduced processing time.

Rathke (*Medical image analysis,* 2014: 18(5): 781-794) proposed a probabilistic approach that models the global shape variations of retinal layers along with their appearance using a variational method. Wang (*J of Comp Inform Sys.* 2015, 11:23, 8467-8475) also segmented 8 retinal layers, but using continuous maximum flow algorithm, that was followed by image flattening based on the detected upper boundary of the outer segment (OS) layer in order to extract the remaining layers' boundaries. Srimathi (*Aust J of Basic and Appl Sci.* 2015, 9:15, 166-171) applied an algorithm for retinal layer segmentation that first reduced speckle noise in OCT images, then extracted layers based on a method that combines active contour model and diffusion maps. Ghorbel (*Patt Recog,* 2011, 44:8, 1590-1603) proposed a method for segmenting 8 retinal layers based on active contours and Markov Random Field (MRF) model. A Kalman filter was also designed to model the approximate parallelism between photoreceptor segments. Dufour (*IEEE Trans. Med. Imag.,* 2013, 32:3, 531-543) proposed an automatic graph-based multi-surface segmentation algorithm that added prior information from a learnt model by internally employing soft constraints. A graph theory approach was also employed by Garvin (*IEEE Trans. Med. Imag,* 2009, 28:9, 1436-1447) for segmenting OCT retina layers, while incorporating varying feasibility constraints and true regional information. Tian (*PloS one,* 2015, 10: 8, e0133908) proposed a real-time automated segmentation method that was implemented using the shortest path between two end nodes. This was incorporated with other techniques, such as masking and region refinement, in order to make use of the spatial information of adjacent frames. Yin (*J of biomed opt,* 2014, 19:8, 086020-086020) applied a user-guided segmentation method that first manually defined lines at irregular regions for which automatic approached fail to segment. Then the algorithm is guided by these traced lines to trace the 3D retinal layers using edge detectors that are based on robust likelihood estimators.

The above discussion demonstrates that there are limitations associated with known retinal layer segmentation OCT-based protocols, for example, low accuracy achieved when having images with low signal to noise ratio (SNR), and the fact that the majority of the proposed approaches could segment only up to eight retinal layers, while methods that segmented more layers were successful only with high-contrast images.

Clearly, an improved OCT retinal segmentation algorithm and analytical model that overcomes these and other deficiencies, and methods for objective and automated monitoring and diagnosis that overcome the inaccuracies and biases associated with current assessment and diagnostic protocols, all remain compelling needs in the art.

SUMMARY OF INVENTION

Accordingly, the present disclosure provides a segmentation algorithm that overcomes these and other deficiencies in the art. Methods for quantifying retinal characteristics and diagnosing ocular pathology are also disclosed. Embodiments of the invention are objective and systematic and may be fully automated and executed by a computer, providing reliable and robust diagnoses and monitoring of even occult retinal conditions and pathologies.

One embodiment provides a retinal OCT segmentation algorithm for constructing a segmentation map of a retinal test OCT image comprising 13 retinal regions. The algorithm comprises: a) providing a probabilistic shape and intensity model derived from a plurality of OCT images generated from control subjects and segmented into 13 retinal regions; b) aligning the test OCT image with the probabilistic shape and intensity model according to retinal region shape; c) comparing aligned pixels of the test OCT image with their corresponding pixels in the control model by intensity, establishing a probable regional fit, and refining regional margins by estimating marginal density distribution with a linear combination a linear combination of discrete Gaussians (LCDG) to generate an initial regional segmentation map of the test OCT image comprising defined retinal regions; and d) fitting the initial segmentation map with a statistical model that accounts for spatial information to achieve a final segmentation map comprising 13 retinal regions. The algorithm may be automated and adapted for execution by a computer.

According to other embodiments, once an OCT image is segmented, diagnostic information from an OCT image may be augmented by quantifying a retinal characteristic from the retinal OCT image data. Methods comprise: obtaining a retinal spectral domain-OCT image from a subject; segmenting the OCT image into layered regions according to a retinal OCT segmentation algorithm, said regions comprising at least the vitreous, the retinal pigment epithelium (RPE) and one or more regions selected from the nerve fiber layer (NFL), ganglion cell layer (GCL), inner plexiform layer (IPL), internal limiting membrane (ILM), inner nuclear layer (INL), outer plexiform layer (OPL), outer nuclear layer (ONL), external limiting membrane (ELM), inner segments (IS), inner/outer segment junction (I/OS), and outer segments of the photoreceptors (OSP); calculating a mean characteristic value within each region; assigning the vitreous region a mean characteristic value equal to zero characteristic units, and assigning the RPE region a mean characteristic level equal to X characteristic units; converting the calculated mean characteristic values for each region based on an offset and uniform scale to yield a control normalized characteristic unit scale from 0 to X; and quantifying the characteristic according to the normalized characteristic unit scale. A characteristic value may be calculated from discrete areas of one or more OCT retinal areas as well. Exemplary areas are selected from left nasal, left temporal, right nasal, right temporal, "left" and "right" being relative to the fovea. Generally, the nasal regional area is closer to the fovea, and an exemplary retinal characteristic is reflectivity.

Additional embodiments provide methods for diagnosing an ocular pathology in a subject. The methods generally comprise: a) obtaining at least one OCT retinal image of the subject; b) quantifying reflectivity in at least one diagnostically relevant retinal region of the subject OCT image; c) comparing the quantified reflectivity value of a retinal region of the subject OCT image to a control reflectivity value for the region derived from either normal control OCT images or pathology-specific control OCT images, to determine a difference if the control reflectivity is derived from normal control subjects, or a fit if the control reflectivity is derived from pathology-specific subjects; d) statistically assessing the difference or fit; and e) diagnosing an ocular pathology if the difference or fit is statistically significant.

Once a subject OCT retinal image is segmented, other features of the OCT image may inform a diagnosis. In other embodiments, thickness and/or curvature of at least one diagnostically relevant retinal region of the subject OCT image may be calculated, along with a mean thickness and/or curvature of the at least one diagnostically relevant retinal region of the control OCT image. The calculated features are compared and a statistical deviation of the subject OCT image retinal region thickness and/or curvature from the control OCT image retinal region thickness and/or curvature is determined, wherein a statistically significant deviation from a normal control or a statistically significant fit to a pathology-specific control indicates a diagnosis of ocular pathology.

In order to eliminate age-bias from a diagnosis, the normal control OCT images and pathology-specific control OCT images may be derived from age-matched subjects. Non-limiting examples of ocular pathologies which may be diagnosed according to embodiments of the invention include age-related macular degeneration (AMD), choroideremia, Stargardt disease, Usher syndrome, diabetic retinopathy, macular hole/pucker, retinoblastoma, retinal detachment, river blindness/onchocerciasis, and retinitis pigmentosa. Methods in accordance with the invention have particular utility in revealing occult conditions of the retina.

Methods of monitoring age-related retinal change in a subject are also disclosed. Generally, the methods comprise: obtaining at least two OCT retinal images of the subject across a longitudinal time frame; quantifying reflectivity of each retinal OCT image in accordance with specific embodiments of the invention, comparing the quantified reflectivity of the images; and monitoring age-related retinal change in the test subject, based on the comparison.

Another embodiment provides methods of monitoring retinal response to treatment of a subject with a pharmaceutical agent. The methods comprise: (a) obtaining a retinal OCT image of at least one retina of the subject prior to initiation of treatment with the pharmaceutical agent; (b) obtaining a retinal OCT image of the at least one retina of the subject after initiation of treatment with the pharmaceutical agent; (c) quantifying reflectivity of each OCT retinal image according to the method of either claim 8 or 9; (d) comparing the quantified reflectivities of step (c) and determining statistically significant differences, and (e) determining a retinal response to treatment where a statistically significant difference is observed.

Still other embodiments provide non-transitory computer readable media storing computer-executable instructions, which when executed by a computer, cause the computer to carry out a method in accordance with the invention.

These and other embodiments will be clarified and better-understood by reference to the Figures and Detailed Discussion set forth below. Although embodiments of the invention are described with particularity, it will be readily understood by a person of ordinary skill in the art that the inventive concepts and principles may be applied in a broader context without departing from the spirit of the invention. The Figures and Examples are set forth to illustrate specific embodiments and should not be construed as limiting the full scope of the invention as defined by the appended claims.

BRIEF DESCRIPTION OF DRAWINGS

FIG. 5A) Segmentation results for different normal OCT images; 5B) segmentation results according to an embodiment of the invention; 5C) segmentation results according to the algorithm/protocols of [20]. The DSC score is displayed above each result.

FIG. 6A) depicts a representative spectral domain (SD)-OCT horizontal raster scan showing the locations from which measurements were taken, 6B) graph showing the raw reflectivity data, 6C) graph showing the normalized reflectivity.

FIG. 9) depicts a table showing mean age, sex, and demographic data by decade of age.

DESCRIPTION OF EMBODIMENTS

Figure 1:
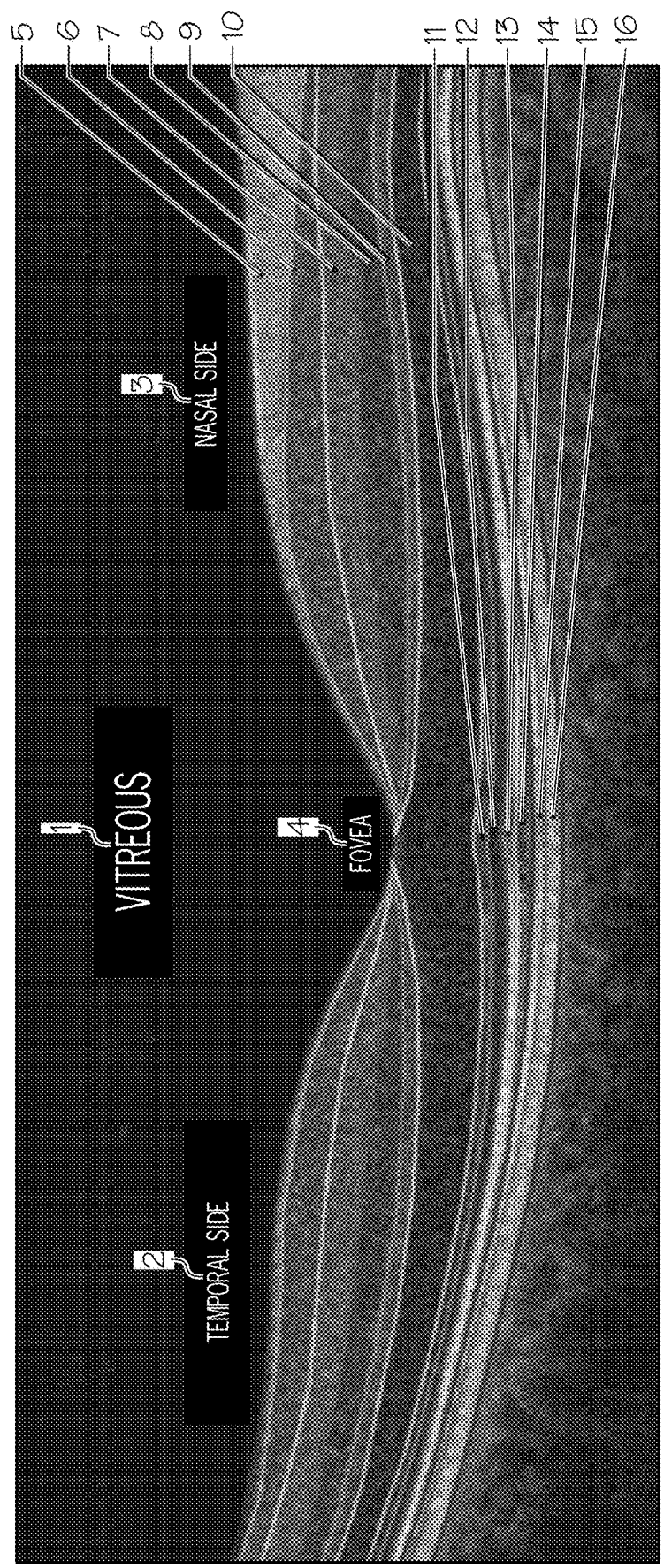
FIG. 1) A typical OCT scan of a normal subject showing 13 distinct retinal regions.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, doses, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "subject" refers to any mammalian subject, including mice, rats, rabbits, pigs, non-human primates, and humans.

Methods according to the invention employ a segmentation model that combines intensity, spatial, and shape information. To the best of the knowledge of the present investigators, this is the first demonstration of a fully automated segmentation approach that has the ability to extract 13 layered retinal regions from an OCT image. This allows, for example the detection of subtle changes that occur in the normal retina with aging, and also permits detection of retinal pathologies prior to clinical manifestation observable by trained specialists.

Embodiments of the invention provide a novel retinal OCT image segmentation algorithm that results in segmentation into 13 distinct, diagnostically relevant layered retinal regions. For purposes of describing particular embodiments, the 13 retinal regions comprise the vitreous, nerve fiber layer (NFL), ganglion cell layer (GC), inner plexiform layer (IPL), internal limiting membrane (ILM), inner nuclear layer (INL), outer plexiform layer (OPL), outer nuclear layer (ONL), external limiting membrane (ELM), inner segments (IS), inner/outer segment junction (I/OS), outer segments of the photoreceptors (OSP), and retinal pigment epithelium (RPE). Once segmented, the investigators discovered that retinal characteristic quantification could be achieved with a high degree of diagnostically-useful saliency when normalized from the vitreous region to the RPE and quantified for the remaining 11 regions. Based on the combined segmentation and characteristic quantification processing of OCT retinal image data, retinal pathologies could be detected at an occult, subclinical stage. Further, the processing is completely objective and systematic such that full automation and thus reliable, fast bedside diagnosis could be achieved based solely on OCT retinal imaging. Further, the objectivity permits elimination of age bias from OCT image data, and eliminates the subjective nature of OCT image analysis by convention manual and hybrid processing techniques.

The computerized automated methods are capable of revealing subtle but clinically significant quantitative characteristics of retinal layer reflectivity. Application of the algorithm to normal eyes across a longitudinal time frame, for example, demonstrates significant changes in retinal layer reflectivity throughout the decades of life and between genders.

The retina, being a direct derivative of the brain, cannot heal and does not regenerate. Currently retinal diseases are detected after substantial anatomical damage to the retinal architecture has already occurred. Successful treatment can only slow disease progression, or at best maintain present visual function. Revealing the normal topographic and age-dependent characteristics of retinal reflectivity and defining rates of normal age-related changes, enables detection of pre-disease conditions and applications in preventive retinal medicine permitting early detection and early treatment of retinal conditions prior to the observation of advanced anatomy-distorting clinical findings.

One embodiment is directed to a novel and highly robust segmentation algorithm for segmenting a test OCT image into 13 distinct retinal regions. Generally the algorithm incorporates shape, intensity and spatial information about the image into a model, which is then used to provide the reference bases to the test OCT segmentation. The algorithm comprises a) providing a probabilistic shape and intensity model derived from a plurality of OCT images generated from control subjects and segmented into 13 retinal regions; b) aligning the test OCT image with the probabilistic shape and intensity model according to retinal region shape; c) comparing pixels of the aligned test OCT image with the corresponding pixels in the control model by intensity, establishing a probable regional fit, and refining regional margins by estimating marginal density distribution with a linear combination a linear combination of discrete Gaussians (LCDG) to generate an initial regional segmentation map of the test OCT image comprising defined retinal regions; and d) fitting the initial segmentation map with a statistical model that accounts for spatial information to achieve a final segmentation map comprising 13 retinal regions.

More specifically, alignment comprises (i) constructing a wavelet decomposition of the test image, (ii) detecting at least three regional boundaries, (iii) identifying the foveal pit by reference to the detected boundaries, (iv) placing fiduciary points (a mark, or one of several marks, visible in the field of view and providing a reference or for measurement) on each detected boundary at locations equidistant from the foveal pit, and (v) aligning the test image to the model image by aligning the fiduciary points. According to very specific embodiments, the statistical model that accounts for spatial information is a Markov-Gibbs Random Field model.

In specific embodiments, the comparing of step comprises (i) constructing a closed set around each aligned test image pixel, (ii) identifying within the set a corresponding model pixel having intensity nearest the image pixel, and, if necessary, expanding the set boundary and/or an intensity tolerance to achieve a non-empty result, and (iii) determining a probability of the aligned test pixel being in one of the 13 retinal regions of the model.

Control subjects or control OCT images derived from control subjects may be normal subjects free of retinal disease or other ocular pathologies. In other embodiments control OCT retinal images are derived from control subjects suffering from a specific retinal pathology, or subjects of a specific demographic profile. In specific embodiments the specific retinal pathology may be any retinal pathology that manifests in some deviation of the OCT retinal image from a normal image. For purposes of describing the algorithms and methods herein, reference is made to very specific retinal disease; however it will be clear to a person of ordinary skill in the art that the algorithms may be applied with predictable efficacy to other ocular pathologies and retinal diseases, so long as the disease is one that is reflected in an OCT retinal image. OCT image analysis is known for many such ocular diseases and conditions, e.g. Schuman, Joel S. "Optical Coherence Tomography of Ocular Diseases," Third Ed. SLACK Inc. (2013) ISBN 10 1-55642-864-2, ISBN 13 978-1-55642-864-7, the entire disclosure of which is incorporated herein by this reference. Controls based on democratic profiles may be matched, for example, by age, gender, race, geographic residence, exposure to environmental factors, ethnicity, and combinations thereof.

Another embodiment of the invention is directed to methods for quantifying a retinal characteristic from retinal OCT image data. The methods initially comprise: (a) obtaining a retinal spectral domain-OCT image from a subject; and (b) segmenting the OCT image into retinal regions according to a retinal OCT segmentation algorithm. The segmented image includes at least the vitreous and the retinal pigment epithelium (RPE) regions, and one or more additional regions selected from the nerve fiber layer (NFL), ganglion cell layer (GCL), inner plexiform layer (IPL), internal limiting membrane (ILM), inner nuclear layer (INL), outer plexiform layer (OPL), outer nuclear layer (ONL), external limiting membrane (ELM), inner segments (IS), inner/outer segment junction (I/OS), and outer segments of the photoreceptors (OSP). A mean raw characteristic value within each region is calculated and the vitreous region is assigned a normalized characteristic value of 0, while the RPE is assigned some value greater than zero, X. X may be selected from any value; however in specific embodiments X is selected from 10, 100 and 1000. In very specific embodiments X is 1000. All calculated raw values are then converted to normalized characteristic units for each retinal region on a scale from 0 to X. The characteristic is then quantified according to the normalized characteristic unit scale for each retinal region.

The normalized reflectivity scale that may be used to interpret and to compare SD-OCT images objectively and in a standard manner. The normalized scale provides a quantifiable measure of OCT scans, which enables the practitioner to objectively perceive pathologic changes before such changes are subjectively appreciated. Further, the normalized scale provides a platform for automated diagnosis of pathology and suggested treatment.

In certain embodiments it may be diagnostically relevant to obtain more than one normalized characteristic scale for the OCT retinal image. For example, different areas of a retinal region may undergo morphological/characteristic changes at different rates. Areas of diagnostic relevance, include for example, left nasal, left temporal, right nasal, right temporal, "left" and "right" being relative to the fovea, nasal being the area closer in anatomical physiology to the nose, and temporal being the side of the fovea farthest from the nose. Clearly these areas will reverse as between the left and right eye.

In very specific embodiments, the retinal characteristic is reflectivity, a characteristic normalized value is a reflectivity unit (RU), and the normalized characteristic unit scale is a normalized reflectivity scale. Any retinal characteristic that is manifest in an OCT retinal image may be quantified accordingly. According to very specific embodiments, the segmentation algorithm is an embodiment of the segmentation algorithm disclosed herein.

Since the measurement is performed in all layers of the retina, there would be a combination of subjective and measurable changes. In addition to having higher or lower reflectivity and difference in the thickness of the layers, some layers might be absent due to the nature of the pathology. The present quantifiable scale provides objective data in a single scan that enhances the ability to differentiate pathologic patterns from normal scans. Application of this approach in diabetic patients shows promising outcomes, which enable the practitioner to detect an ocular pathology before it is evident subjectively.

Utilizing the novel normalized reflectivity scale provides an alternate method of observing the progressive structural changes that occur within the retina as a function of age, and also offers a new way to gain quantitative data from OCT images. As shown in FIG. 7A-I, significant previously unrecognized changes in the reflectivity of the ellipsoid and nerve fiber layers that occur with normal aging in a population of patients with non-pathological retinas were demonstrated. The presently disclosed novel scale allows each layer to be identified and normalized to an age matched group.

Other embodiments are directed to methods of diagnosing an ocular pathology in a subject utilizing the novel segmentation algorithm followed by quantification of a retinal characteristic. The methods comprise obtaining at least one OCT retinal image of the subject; quantifying reflectivity in at least one diagnostically relevant retinal region of the subject OCT image according to embodiments disclosed herein; comparing the quantified reflectivity of the retinal region of the subject OCT image to a control quantified reflectivity derived from either normal control OCT images or pathology-specific control OCT images, to determine a difference if the control reflectivity is derived from normal control subjects, and a fit if the control reflectivity is derived from pathology-specific subjects; statistically assessing the difference or fit; and diagnosing an ocular pathology if the difference or fit is statistically significant.

Other retinal characteristics observable on an OCT retinal image may also inform a diagnosis. In specific embodiments, the methods further comprise: calculating thickness and/or curvature of at least one diagnostically relevant retinal region of the subject OCT image; calculating a mean thickness and/or curvature of the at least one diagnostically relevant retinal regions of the control OCT images; comparing the calculations; and determining a statistically significant difference or fit of the subject OCT image retinal region thickness and/or curvature over the control OCT image retinal region thickness and/or curvature, wherein a statistically significant difference from a normal control or a statistically significant fit to a pathology-specific control indicates a diagnosis of ocular pathology. Methods for determining thickness and curvature of an OCT retinal region are well-known in the art.

Specific ocular pathologies which may be assessed or diagnosed by the instant methods include those in which image texture or reflectivity are known to vary with disease and disease/condition progression. Non-limiting examples include age-related macular degeneration (AMD), choroideremia, Stargardt disease, Usher syndrome, diabetic retinopathy, macular hole/pucker, retinoblastoma, retinal detachment, river blindness/onchocerciasis, and retinitis pigmentosa.

The present investigators surprisingly found that certain diseases may be detected at very early occult and pre-clinical stages by implementing embodiments of the novel methods disclosed herein. For example, patients suffering from diabetes are at risk for developing diabetic retinopathy; however modern clinical procedures do not detect retinopathy until irreversible damage has occurred. Diabetic retinopathy, even in the absence of overt clinical symptoms, was found to be indicated where: (i) subject OCT image normalized reflectivity values derived in accordance with embodiments of the disclosed methods are greater than the normal control OCT image normalized reflectivity values for a majority of retinal regions, and/or (ii) subject normalized reflectivity values within at least one retinal region differ significantly between left and right regional areas, and/or (iii) curvature and thickness of subject OCT segmented retinal regions vary by retinal region and by left and right regional area for at least two retinal regions. In very specific embodiments, the two retinal regions comprise the IPL and the INL.

Glaucoma may also be detected/diagnosed prior to manifestation of overt clinical symptoms. According to embodiments of the inventive methods, a diagnosis of glaucoma is indicated where: (i) subject OCT image normalized reflectivity values in the NFL retinal region are greater than normal control OCT image normalized reflectivity values in the NFL retinal region, and (ii) subject OCT image thickness of the NFL retinal region is less than normal control OCT image thickness of the NFL retinal region.

It is well known that the normal retina undergoes age-related retinal change. Such changes may be monitored for signs of extreme/clinical changes by utilizing method embodiments of the instant disclosure. In specific embodiments, the method comprises: obtaining at least two OCT retinal images of the subject across a longitudinal time frame; segmenting and quantifying reflectivity of each retinal OCT image in accordance with the disclosed methods, comparing the quantified reflectivity of the at least two OCT retinal images; and monitoring age-related retinal change in the test subject, based on the comparison.

Other embodiments provide methods for managing an age-related chorioretinal disease in a subject. Generally, at least a first OCT retinal image and a second OCT retinal image of the subject across a longitudinal time frame are obtained, reflectivity is quantified for each OCT retinal image according to embodiments of the novel methods, and the quantified reflectivity of the first OCT retinal image is compared with the quantified reflectivity of the second OCT retinal image. The age-related chorioretinal disease may be managed based on the comparison. In very specific embodiments, the age-related chorioretinal disease is associated with neovascular age-related macular degeneration. In other specific embodiments, age-related macular degeneration is managed to reduce the rate of change of reflectivity of retinal regions.

Methods of monitoring retinal response to treatment of a subject with a pharmaceutical gent are also provided. A retinal OCT image of at least one retina of the subject is obtained prior to initiation of treatment with the pharmaceutical agent, and at least one retinal OCT image of the at least one retina of the subject is obtained after initiation of treatment with the pharmaceutical agent. The reflectivity of each OCT retinal image is quantified in accordance with embodiments of the invention, and the quantified reflectivities are compared and the differences are statistically analyzed for significant or trending differences. A retinal response to treatment is determined where a statistically significant difference is observed. Where macular remodeling is a treatment goal, subclinical indications of remodeling may be detected by implementing the present methods. In another specific example, the subject suffers from glaucoma and the retinal response is cessation or reversal of nerve fiber layer (NFL) atrophy.

The present inventive methods are highly advantageous in that they enable automatic and reliable diagnoses and assessment by non-practitioners as well as practitioners. The ability to read an OCT retinal image is not required and the methods are readily automated for execution by a computer. One embodiment provides a non-transitory computer readable media storing computer-executable instructions, which, when executed by a computer, cause the computer to carry out a method comprising: receiving a test OCT image of a retina; segmenting the test OCT image into 13 retinal regions based on a retinal OCT image model incorporating shape, intensity and spatial information derived from a control group of OCT images, wherein the 13 retinal regions comprise: vitreous, nerve fiber layer (NFL), ganglion cell layer (GC), inner plexiform layer (IPL), internal limiting membrane (ILM), inner nuclear layer (INL), outer plexiform layer (OPL), outer nuclear layer (ONL), external limiting membrane (ELM), inner segments (IS), inner/outer segment junction (I/OS), outer segments of the photoreceptors (OSP), and retinal pigment epithelium (RPE), further wherein reflectivity of each retinal region is quantified with a reflectivity unit value according to a normalized reflectivity scale; deriving a normalized reflectivity scale for the test OCT image and assigning a reflective unit value to each retinal region based on the normalized reflectivity scale; comparing the assigned reflective unit values of each retinal region of the test OCT image to the model reflective unit values for the same retinal regions; and diagnosing a retinal pathology by correlating the comparison result with a database of retinal pathologies associated with normalized reflectivity scales specific to each retinal pathology. Exemplary programming is illustrated in Example 6. Further, FIG. 2 sets forth a schematic operation flow for automated/computerized performance of embodiments of the inventive methods.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. The following Examples are set forth to illustrate particular embodiments and should not be construed as limiting the scope, which is defined by the appended claims.

Example 1

This example illustrates development of a retinal SD-OCT segmentation algorithm in accordance with embodiments of the invention.

A. Data Collection

Subjects were recruited at the Kentucky Lions Eye Center, University of Louisville Department of Ophthalmology and Visual Sciences, Louisville, Ky. between June 2015 and December 2015. Informed consent was obtained from all participants. Subjects with normal retinas ranging in age from 10 to 79 years old were included in the study. Past medical history, ophthalmologic history, smoking status, and current medications were obtained via chart review and subject interview. Persons with history significant for any retinal pathology, history significant for diabetes mellitus, high myopia defined as a refractive error greater than or equal to −6.00 diopters, and tilted OCT image were excluded from participation in the study. SD-OCT scans were prospectively collected from 165 normal subjects using the Zeiss Cirrus HD-OCT 5000. SD-OCT data were exported for analysis as 8-bit, greyscale raw files with size 1024 pixels×1024 pixels×N slices, where N=5 or 21. For N=5, the field of view as 6 mm nasal-temporal (N-T) and 2 mm posterior-anterior (P-A), and the slice spacing was 0.25 mm.

For N=21, the field of view was 9 mm N-T and 2 mm P-A, while the slice spacing was 0.3 mm.

B. Automatic Segmentation of Twelve Retinal Layers

Let g×{g(x): x∈R; g(x)∈Q} and m={l(x): x∈R; l(x)∈L} be a grayscale image taking values from Q, i.e. g: R→Q, with the associated region map taking values from L, i.e. m: R→L, respectively. R denotes a finite arithmetic lattice, Q is a finite set of integer gray values, and L is a set of region labels. An input OCT image, g, co-aligned to the training database, and its map, m, are described with a joint probability model:

$$P(g,m)=P(g|m)P(m). \quad (1)$$

The joint probability model combines a conditional distribution of the images given the map P(g|m), and an unconditional probability distribution of maps $P(m)=P_{sp}(m)P_V(m)$. Here, $P_{sp}(m)$ denotes a weighted shape model, and $P_V(m)$ is a Gibbs probability distribution with potentials V, that specifies a MGRF model of spatially homogeneous maps m.

(iv) Adaptive Shape Model $P_{sp}(m)$

In order to account for the inhomogeneity of the OCT images, the shape information is taken into account in the segmentation. The shape model is built using 12 OCT scans, selected from 6 men and 6 women. "Ground truth" segmentations of these scans were delineated under supervision of retina specialists. Using one of the optimal scans as a reference (no tilt, centrally located fovea), the others were co-registered using a thin plate spline (TPS) (see J. Lim and M.-H. Yang; "A direct method for modeling non-rigid motion with thin plate spline" *CVPR*, 2005, pp. 1196-1202, the disclosure of which is incorporated herein by this reference). The shape model is defined as:

$$P_{sp}(m)=\Pi_{y \in R} P_{sp:y}$$

Where y is the image pixel with gray level g. The same deformations were applied to their respective ground truth segmentations, which were then averaged to produce a probabilistic shape model of the typical retina, i.e., each position x in the reference space is assigned a prior probability P(m) to lie within each of the 12 tissue classes.

Figure 3A:
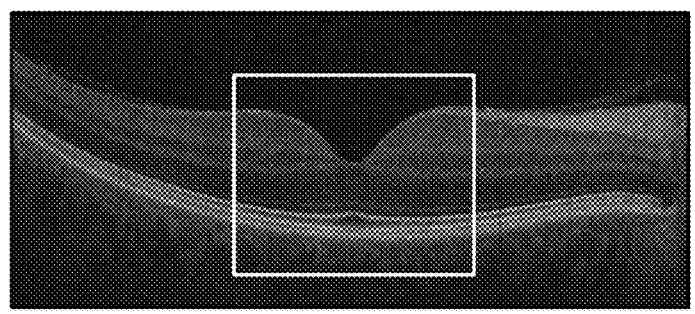
FIG. 3A) Shows a bounded region of an OCT image for wavelet decomposition-based edge-tracking of 3B) large scale structure of the retina; 3C) image depicting the multiscale edges near the foveal peak, inside the bounded region; 3D) image showing three boundaries detected after alignment.
Figure 3B:
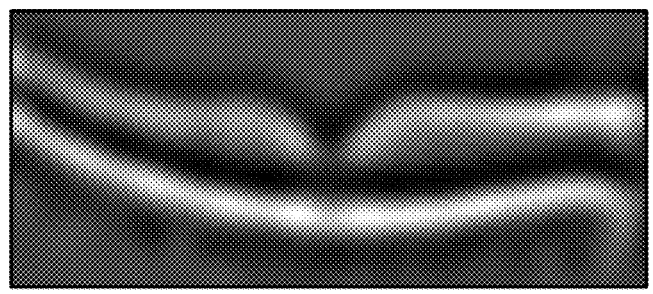
Figure 3C:
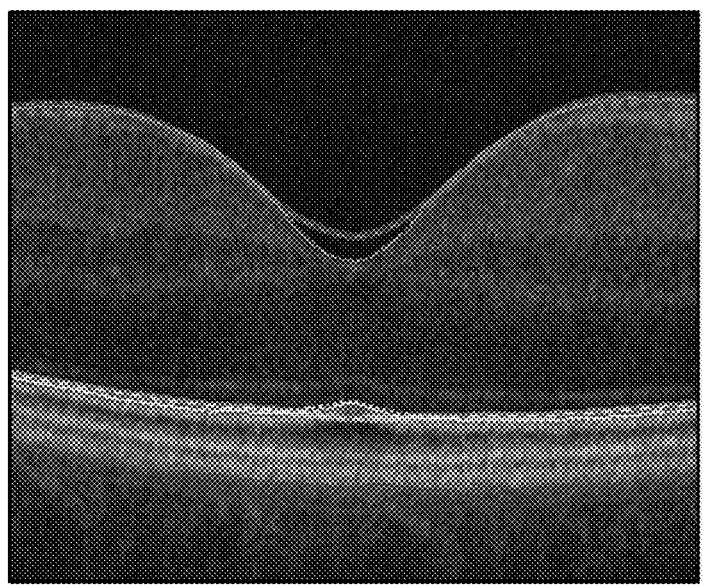
Figure 3D:
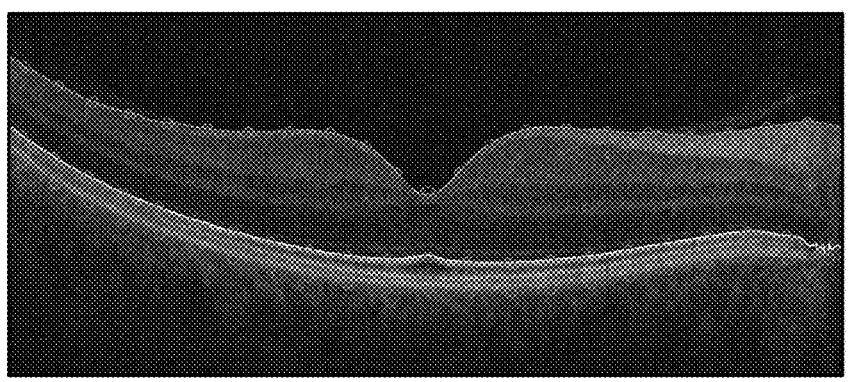
Figure 4A:
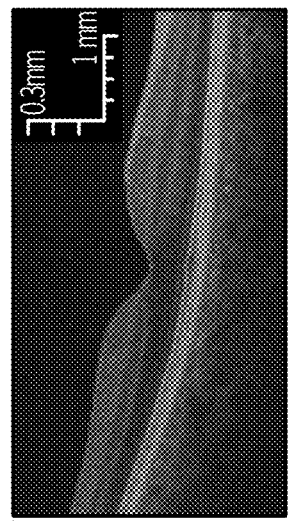
FIG. 4A) representative OCT image of a 65 year-old female, 4B) edge tracking with wavelet decomposition, 4C) co-alignment using TPS control points, 4D) LCDG-modes for different layers, 4E) segmentation after using the joint MGRF model, and 4F) overlaid layer edges on the original image.
Figure 4B:
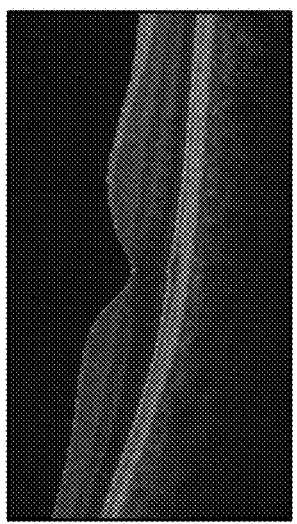
Figure 4C:
Figure 4D:
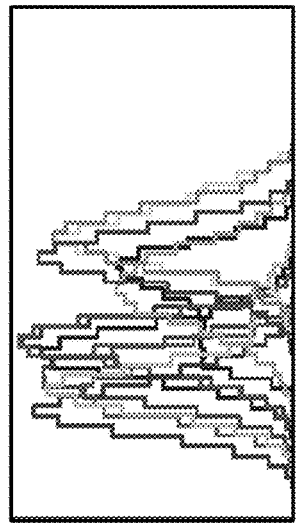
Figure 4E:
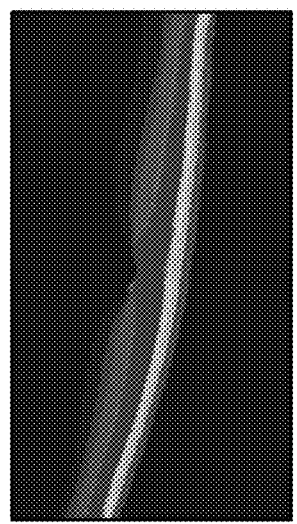
Figure 4F:
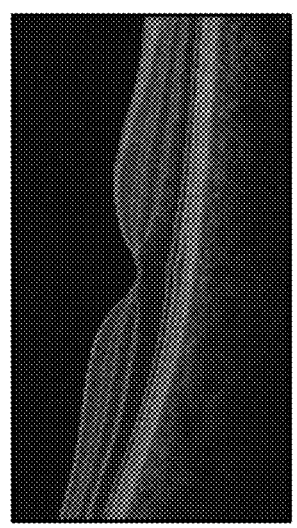

In order to segment the input image, it must be first aligned (registered) to the shape model. In accordance with one embodiment, an alignment approach is provided that integrates TPS with multi-resolution edge tracking method that identifies control points for initializing the alignment process. First, The "'a trous" algorithm (see Lega E, Scholl H, Alimi J-M, Bijaoui A, and Bury P. A parallel algorithm for structure detection based on wavelet and segmentation analysis. *Parallel Comput.*, 1995, 21: 2, pp. 265-285, 1995, the entire disclosure of which is incorporated by this reference) was used to build a wavelet decomposition of each scan. At a coarse enough level of detail, the retina takes on a three-banded appearance, with two hyperreflective bands separated by a hyporeflective band corresponding roughly to layers from ONL to MZ. Contours following the gradient maxima of this wavelet component provided initial estimates of the vitreous/NFL, MZ/EZ, and RPE/choroid boundaries, FIG. 3D. The fourth gradient maximum could estimate the OPL/ONL boundary, but that is not sharp enough an edge to be of use. These ridges in gradient magnitude were followed through scale space to the third wavelet component, corresponding to a scale of approximately 15 micrometers for the OCT scans used in the study.

The foveal pit was then determined as the point of closest approach of the vitreous/NFL and MZ/EZ contours. Control points were then located on these boundaries at the foveal pit and at uniform intervals nasally and temporally therefrom.

Finally, the optimized TPS was employed in order to align the input image to the shape database using the control points identified.

(v) First-Order Intensity Model P (g|m)

In order to make the segmentation adaptive and not biased to only the shape information, the empirical gray level distribution of the OCT images was modeled. The first-order visual appearance of each label of the image is modeled by separating a mixed distribution of pixel intensities into individual components associated with the dominant modes of the mixture. The latter is approximated using the LCDG approach (El-Baz A, Elnakib A, Khalifa F, El-Ghar M A, McClure P, Soliman A, and Gimelrfarb G. "Precise segmentation of 3D magnetic resonance angiography"; *IEEE Trans. Biomed. Eng.* 2012, 59: 7, pp. 2019-2029), which employs positive and negative Gaussian components that are based on a modified version of the classical Expectation Maximization (EM) algorithm. Let $\psi_\theta=(\psi(q|\theta): q \in Q)$ denote discrete Gaussian (DG) with parameters $\theta=(\mu, \sigma)$, integrating a continuous 1D Gaussian density with mean $\mu$ and variance $\sigma^2$ over successive gray level intervals. The LCDG with four dominant positive DGs and $C_p \geq 4$ positive and $C_n \geq 0$ negative subordinate DGs is:

$$P_{\omega,\theta}(q|m)=\Sigma_{k=1}^{C_p}\omega_{p:k}\psi(q|\theta_{p:k})-\Sigma_{k=1}^{C_n}\omega_{n:k}\psi(q|\theta_{n:k})$$

Where m takes one of the labels from 1 to 12, and all the weights $w=[\omega_{p:k},\omega_{n:k}]$ are non-negative and meet an obvious constraint $\Sigma_{k=1}^{C_p}\omega_{p:k}-\Sigma_{k=1}^{C_n}\omega_{n:k}=1$.

(vi) Second-Order Spatial MGRF Model $P_V(m)$

In order to improve the spatial homogeneity of the segmentation, the MGRF Potts model that accounts for spatial information was incorporated with the shape and intensity information (Alansary A, Ismail M, Soliman A, et al. "Infant brain extraction in T1-weighted MR images using BET and refinement using LCDG and MGRF models"; *IEEE J Biomed Health Inform.* 2015). This model is identified using the nearest pixels' 8-neighborhood $v_s$ and analytical bi-valued Gibbs potentials as:

$$P(m)\alpha \exp(\Sigma_{(x,y) \in R}\Sigma_{\xi,\zeta}V(l_{x,y},l_{x+\xi,y+\zeta}))$$

Where V is the bi-value Gibbs potential that depends on the equality of the nearest pair of labels:

$$V = \begin{cases} V(\lambda, \hat{\lambda}) = V_{eq} & \text{if } \lambda = \hat{\lambda} \\ V(\lambda, \hat{\lambda}) = V_{ne} & \text{if } \lambda \neq \hat{\lambda} \end{cases}$$

The initial m results in approximate analytical maximum likelihood potentials estimates:

$$V_{eq}=-V_{ne}\approx 2f_{eq}(m)-1$$

That allow for computing the pixel-wise probabilities $p_{x,y}(l_{x,y}=\lambda)$ of each label $\lambda \in L$.

Figure 2A:
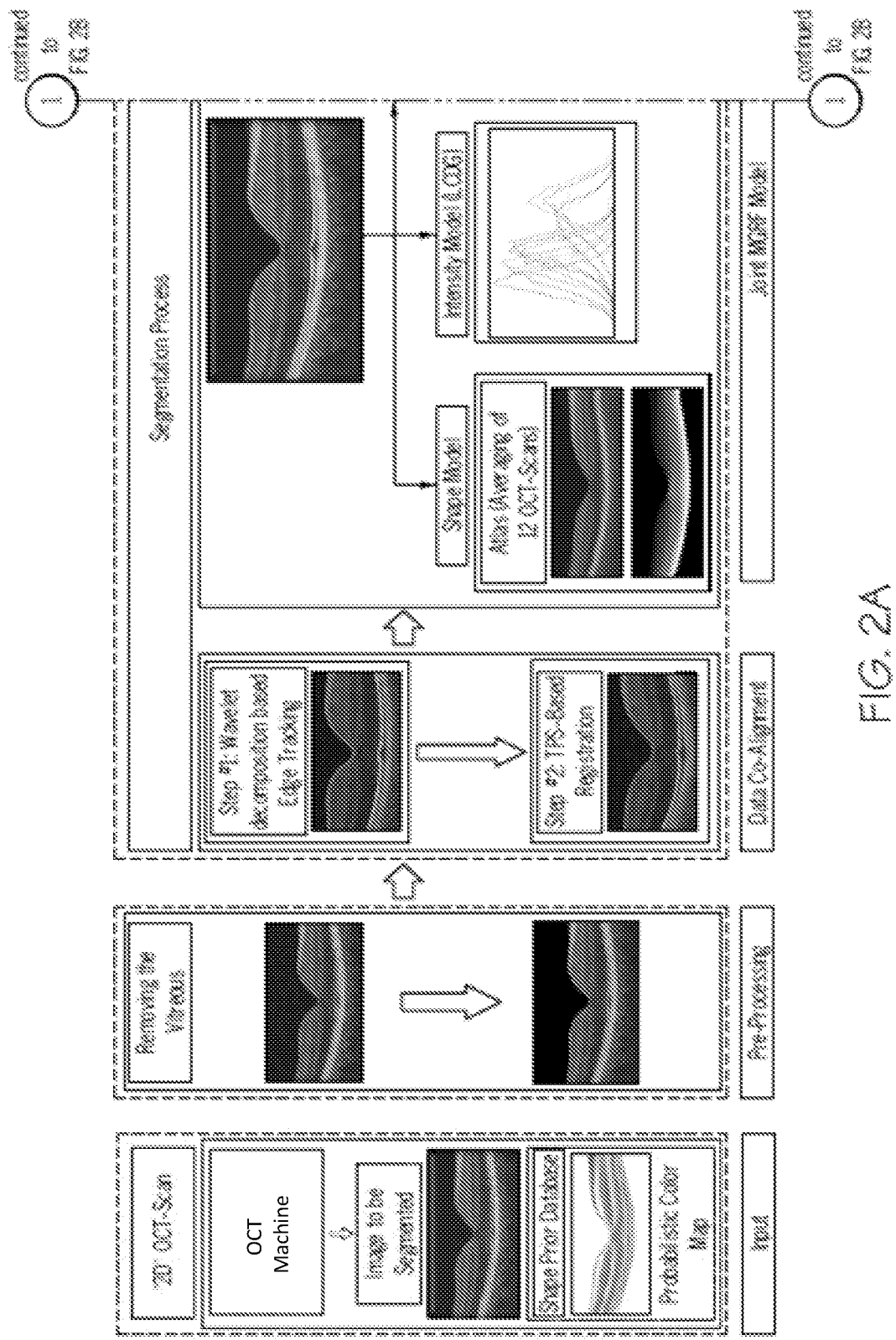
FIG. 2A) First part of schematic of the basic steps of the proposed OCT segmentation framework; 2B) second part of schematic of basic steps of the proposed OCT segmentation framework.
Figure 2B:
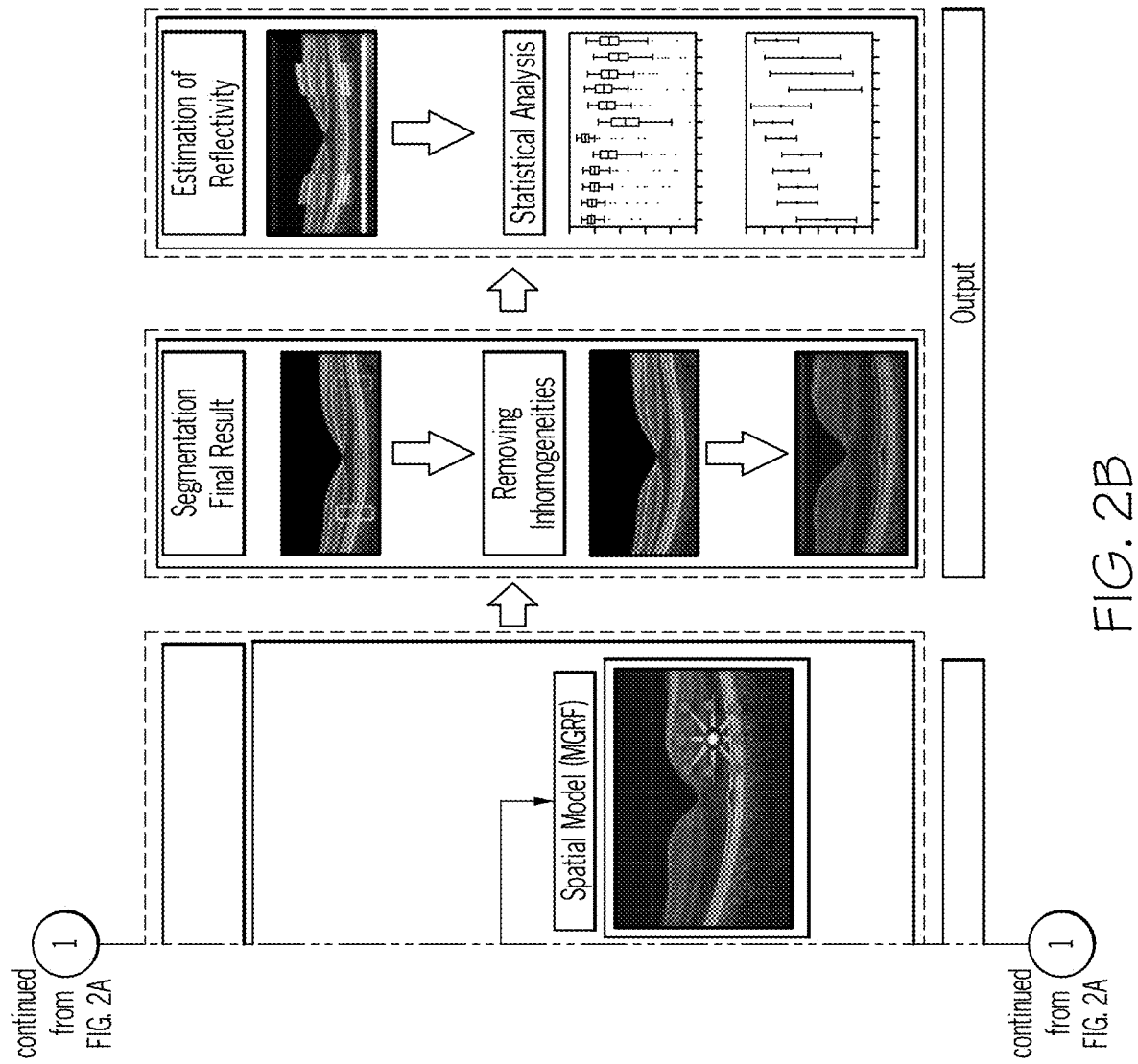

The steps of the segmentation framework are illustrated in FIG. 2. Images showing application of the segmentation framework are set forth in FIG. 3 and FIG. 4.

The performance of the proposed segmentation framework relative to manual segmentation was evaluated using the agreement coefficient ($AC_1$) and the Dice similarity coefficient of similarity ($F_1$) DSC (Gwet K L. Computing inter-rater reliability and its variance in the presence of high agreement. *Bri J Math Stat Psychol.* 2008; 61:29-48; S. J. Chiu, X. T. Li, P. Nicholas, C. A. Toth, J. A. Izatt, and S. Farsiu, "Automatic segmentation of seven retinal layers in SDOCT images congruent with expert manual segmentation."

An outline of application of the segmentation algorithm to analysis of an OCT test image is set forth below.

I—Pre-Processing
11. Load the shape model (atlas) along with the test image.

II—Alignment of the Test Image with the Shape Model/Atlas:
12. Use an "a trous" algorithm to construct wavelet decomposition of the input image, and locate the vitreous/NFL, IPL/EL, and RPE/choroid boundaries.
13. Identify the foveal pit using the 3 detected boundaries.
14. Place fiducial points on each detected boundary, starting at the foveal pit and moving outward at equidistant intervals.
15. Align the input image to the atlas using the control points identified.

III—Initial Segmentation:
16. Initialize a 2D window of size N1×N2 centered on each aligned pixel, and search within for the atlas pixel having intensity nearest the image pixel.
17. Increase the window size, if needed, and redo the search until a non-empty result is found. If maximum size is reached and no result is found, increase the intensity tolerance and get back to previous step.
18. Look up in the atlas the prior probability of the corresponding pixel belonging to each class.

IV—Final Segmentation:
19. Approximate the marginal intensity distribution P(g) of the OCT image using an LCDG with four dominant modes.
20. Form an initial region map m using the marginal estimated density and prior shape of each label.
21. Find the Gibbs potentials for the MGRF model (for pairwise and higher-order cliques) from the initial map m. Obtain the final segmentation using the joint probability model in Equation 1.

Step-by-step demonstration showing application of the proposed segmentation approach for a normal subject is shown in FIG. 4. First, the edges of the input OCT image (FIG. 4A) is tracked using wavelet decomposition method (FIG. 4B) and is followed by its co-alignment to the shape database using identified TPS control points (FIG. 4C). Initial segmentation result is first obtained using the shape model (FIG. 4D) then refined using the joint-MGRF model to obtain the final segmentation result (FIG. 4E). Additional segmentation results for normal subjects are demonstrated in FIG. 5.

The robustness and accuracy of the method is evaluated using both AC1 and DSC metrics, and the AD distance metric comparing the segmentation with the ground truth. Comparison with 165 manually segmented scans found the mean boundary error was 6.87 micrometers, averaged across all 13 boundaries; the inner (vitreous) boundary of the retina was placed most accurately, with 2.78 micrometers mean error. The worst performance was on the outer (choroid) boundary, with mean deviation of 11.6 micrometers from ground truth. The AC1 gives mean of 77.2% with standard deviation 4.46% (robust range 64.0%-86%). Some layers were more accurately automatically segmented than others (FIG. 4A-F), with Dice coefficient of similarity as high as 87.8% with standard deviation of 3.6% in the outer nuclear layer (robust range 79.2%-95.1%) but low as 58.3% with standard deviation of 13.1% in the external limiting membrane.

Example 2

This example illustrates derivation of quantitative data from segmented SD-OCT images in accordance with an embodiment of the invention. In particular the concept is illustrated utilizing reflectivity as the quantified characteristic and development of a normalized reflectivity scale.

Quantitative Data Derived from SD-OCT Images

Several quantitative data can be derived from the segmented SD-OCT images in order to optimally characterize retinal morphology. Specific embodiments herein are described in terms of the reflectivity measurements that were obtained from two regions per scan, comprising the thickest portions of the retina on the nasal and temporal sides of the foveal peak. Although the embodiment is described and illustrated utilizing reflectivity, it will be apparent to the person of skill in the art that the methods are applicable for other quantifiable retinal characteristics.

Mean reflectivity is expressed on a normalized scale, calibrated such that the formed vitreous has a mean value of 0 NRS, and the retinal pigment epithelium has a mean value of 1000 NRS. The average grey level within a segment was calculated using Huber's M-estimate, which is resistant to outlying values that may be present, such as very bright pixels in the innermost segment that properly belong to the internal limiting membrane and not the NFL. Average grey levels were converted to NRS units via an offset and uniform scaling. Statistical analysis employed ANCOVA on a full factorial design with factors gender, side of the fovea (nasal or temporal) and retinal layer, and continuous covariate age.

Example 3

This example illustrates application of an embodiment of the automated segmentation algorithm to an analysis of retinal layer reflectivity as a function of gender, age, and demographic. The reflectivity unit (RU) data is summarized by age in FIG. 9.

After the segmentation protocol is applied to the collected images, analysis of the reflectivity measure across the different decades of life is undertaken. Embodiments of the segmentation approach were first validated using "ground truth" for subjects, which was collected from 165 subjects aged 10-79 years. Subjects with high myopia (≤−6.0 diopters), and tilted OCT were excluded. This ground truth was created by manual delineations of retina layers reviewed with 4 different retina specialists (SS, AP, AH, DS).

This study was reviewed and approved by the Institutional Review Board at the University of Louisville. A retrospective chart review was performed to identify subjects between 13 and 97 years of age without significant ocular pathology. Data collected included age, sex, visual acuity, and past medical and ocular histories. Subjects included in the study were individuals with no systemic diseases including hypertension and diabetes, visual acuity of 20/40 or better and without clinical evidence of any ocular pathology. Exclusion criteria were ophthalmic pathology diagnoses including, but not limited to, diabetic retinopathy, age-related macular degeneration, glaucoma, cystoid macular edema, and epiretinal membrane, or a history of retinal surgery including laser treatments. Remaining patients (n=179) were subsequently divided into nine age groups representing each decade of life (10-19, 20-29, 30-39, 40-49, 50-59, 60-69, 70-79, 80-89, and 90-99 years). Raw spectral domain OCT (SD-OCT, Spectralis SLO-OCT, Heidelberg Engineering, Heidelberg, Germany) data taken from horizontal line scans of each patient was imported into ImageJ (version 1.48; National Institutes of Health, Bethesda, Md., USA) for further analysis. The vitreous and all retinal layers were measured both nasally and temporally to the fovea between 50 µm and 300-400 µm from the foveal center in either direction. A normalized reflectivity scale (NRS) was established for OCT reflectivity ranging from 0 units (defined as the reflectivity of the vitreous) to 1000 units (defined as the reflectivity of the RPE). Raw reflectivity in the nasal and temporal parafovea was measured with ImageJ, converted to NRS, and compared for all retinal layers.

Statistical Analysis

Statistical analysis was carried out using statistical software (SPSS version 17.0; SPSS, Inc., Chicago, Ill., USA). Multivariate analysis was performed using two-way ANOVA analysis. Values were considered significant if P<0.05.

Results

A total of 323 eyes of 179 subjects (87 males and 92 females) were included. NRS of the nerve fiber layer (NFL) showed significantly higher reflectivity in the nasal parafoveal retina as compared to temporal side (843 vs 559 units; P<0.001). None of the other retinal layers demonstrated a statistically significant difference between the nasal and temporal sides (FIG. 7A-7I). The NRS-NFL decreased throughout life and became significantly different from baseline (age group 10-19) in age group 30-39 on the nasal side (1168 vs 882 units; P<0.001) and in age group 70-79 on the temporal side (673 vs 483 units; P=0.02). There were statistically significant correlations with aging in the NFL and ellipsoid layer (P<0.001). All other layers did not significantly change in NRS scale with age.

The subjects mean age was 60.3+/−19.6 years (FIG. 9). There was no significant difference in the visual acuity of the patients in different age groups.

To demonstrate the changes in reflectivity of retinal layers, each raster scan was normalized to the raw reflectivity of the vitreous and RPE. In addition, the ratio of raw reflectivity of the RPE to vitreous showed no significant changes in normal subjects throughout the groups.

Figure 7A:
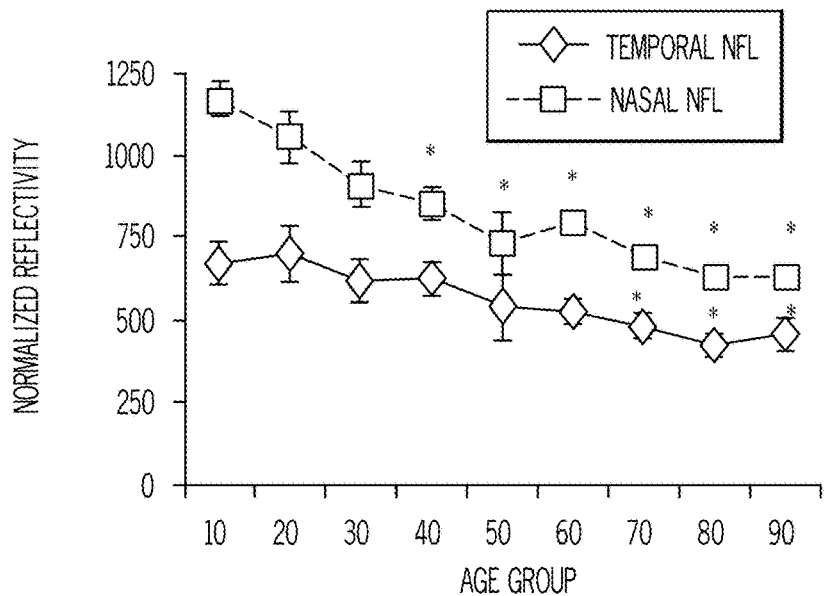
FIG. 7A) shows normalized reflectivity plotted against decade of life for the temporal and nasal regions of the NFL, showing that the NFL measured differently in nasal vs. temporal locations, 7B) shows normalized reflectivity plotted against decade of life for the temporal and nasal regions of the Ganglion, 7C) shows normalized reflectivity plotted against decade of life for the temporal and nasal regions of the IPL, 7D) shows normalized reflectivity plotted against decade of life for the temporal and nasal regions of the INL, 7E) shows normalized reflectivity plotted against decade of life for the temporal and nasal regions of the OPL, 7F) shows normalized reflectivity plotted against decade of life for the temporal and nasal regions of the ONL, 7G) shows normalized reflectivity plotted against decade of life for the temporal and nasal regions of the ELM, 7H) shows normalized reflectivity plotted against decade of life for the temporal and nasal regions of the IS, and 7I) shows normalized reflectivity plotted against decade of life for the temporal and nasal regions of the Ellipsoid. All layers except the NFL showed symmetric NRS values with respect to the fovea (B-I). (*$P<0.01$ compared to age matched group 10-19).
Figure 7B:
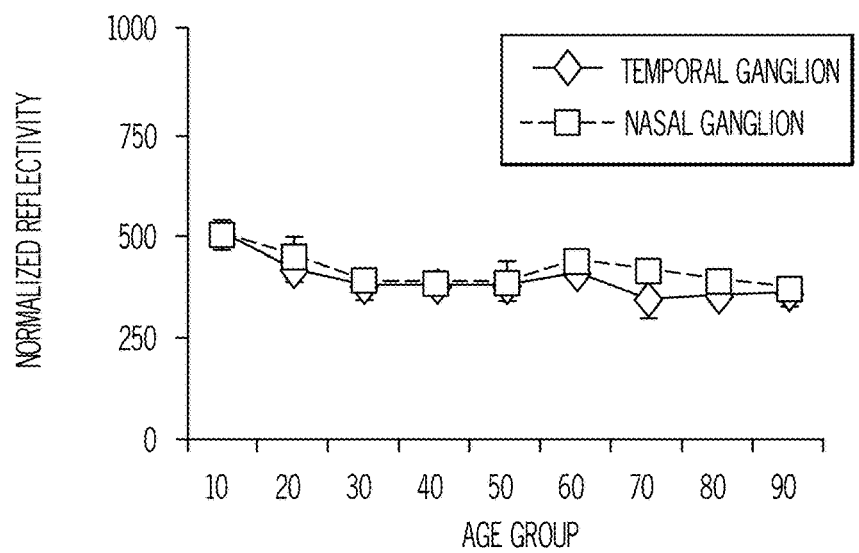
Figure 7C:
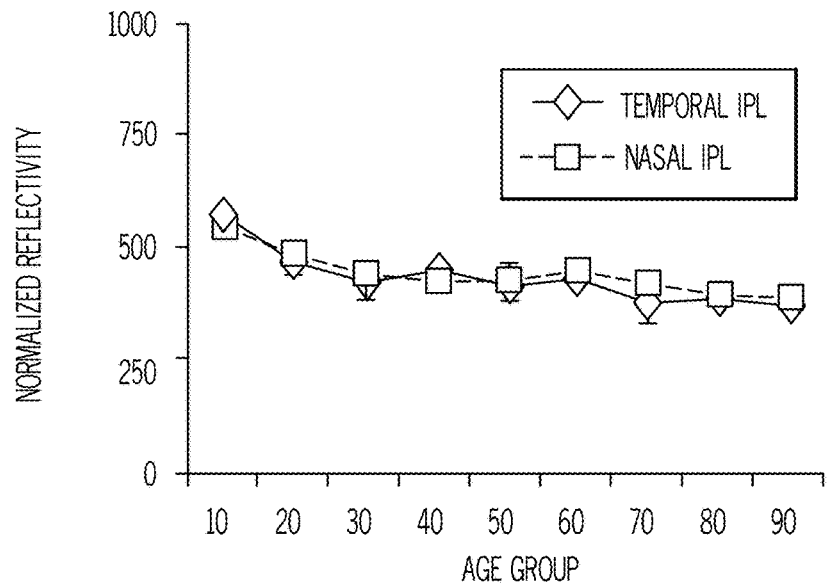
Figure 7D:
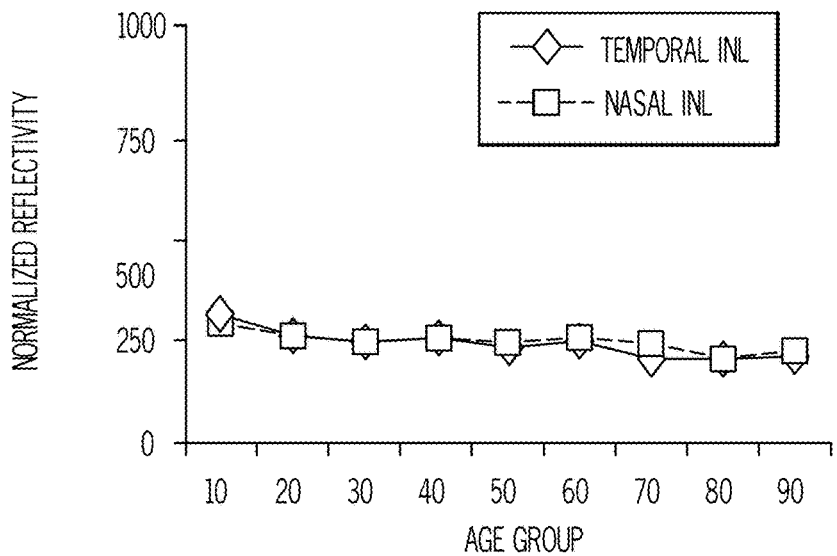
Figure 7E:
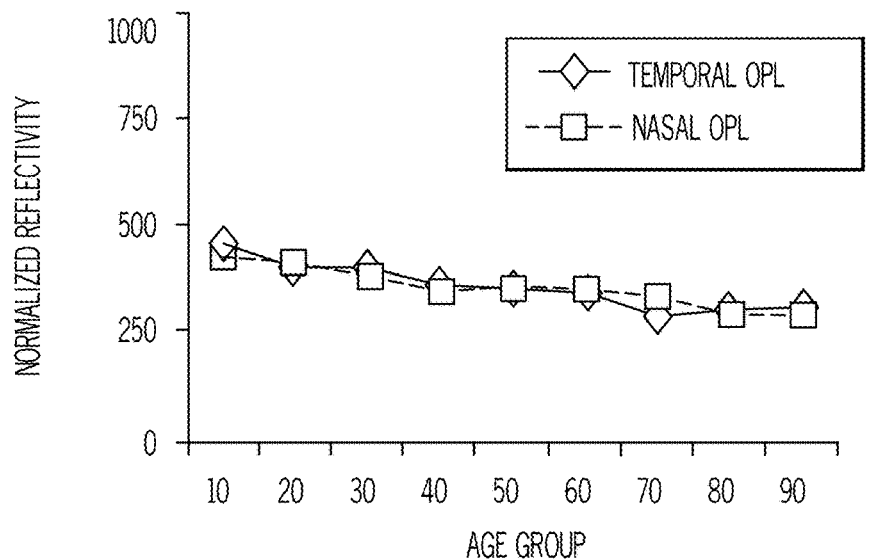
Figure 7F:
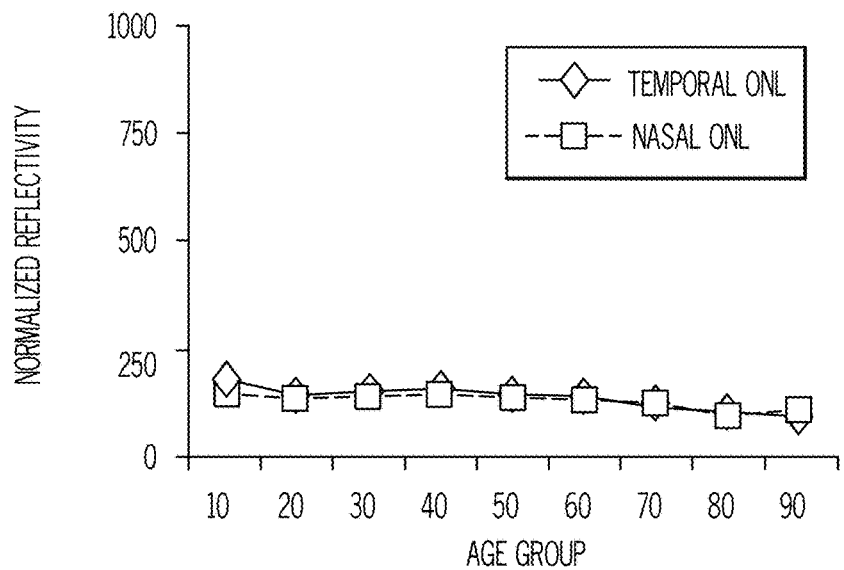
Figure 7G:
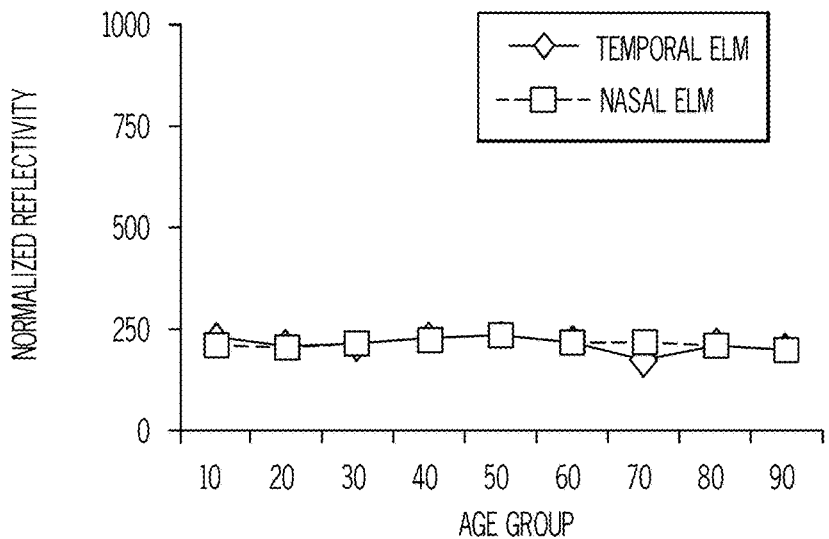
Figure 7H:
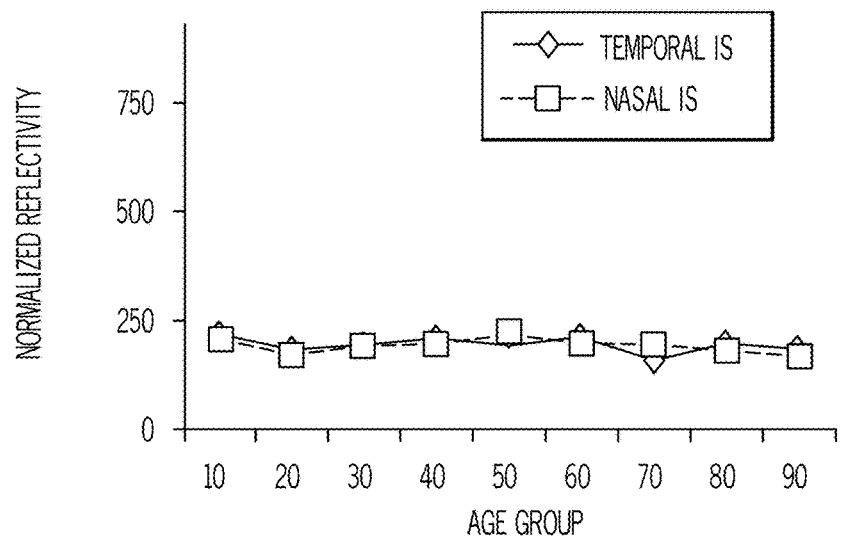
Figure 7I:
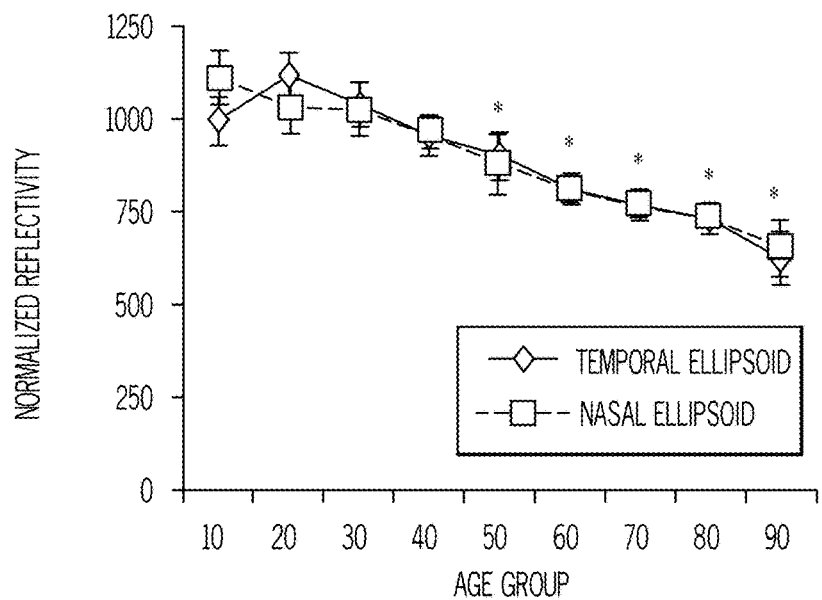
Figure 8A:
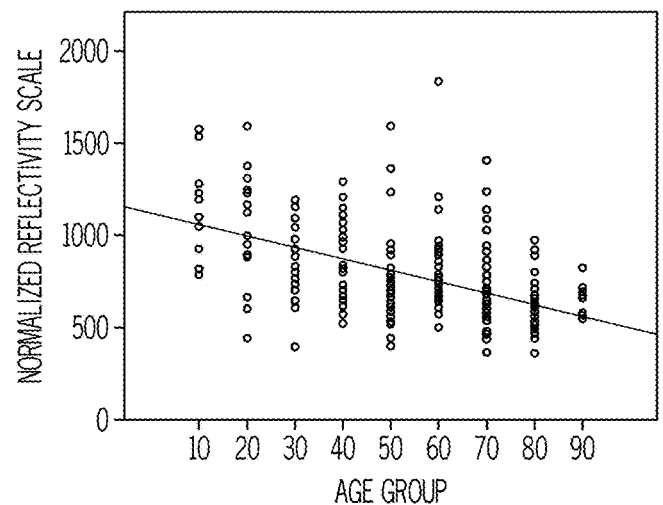
FIG. 8A) shows normalized reflectivity score (NRS) plotted against decade of life for the nasal zone of the NFL; 8B) shows NRS plotted against decade of life for the temporal zone of the NFL; 8C) shows NRS plotted against decade of life for the ellipsoid zone. Both of the nerve fiber layer zones and the ellipsoid zone showed a significant decrease in NRS with age. No other retinal layers shared this reduction in NRS.
Figure 8B:
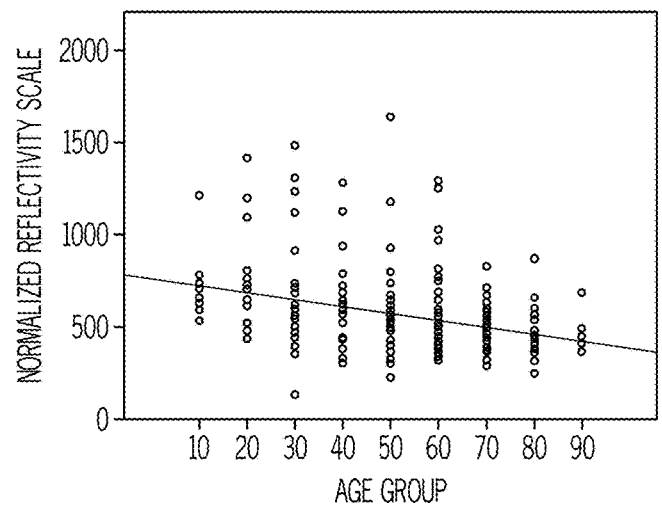
Figure 8C:
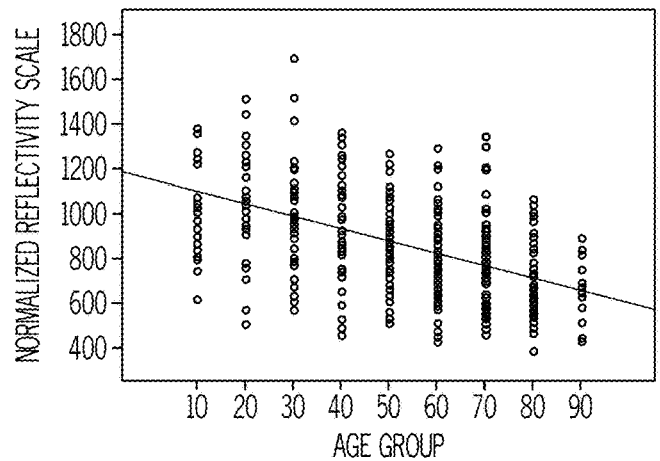

The changes in NRS with age and location within the retina are shown in FIGS. 7A and 8. Comparison of NRS nasal and temporal to the fovea showed that the reflectivity of the nerve fiber layer (NFL) was significantly higher in the nasal parafoveal retina as compared to the temporal side (843 vs 559 units; P<0.001). None of the other retinal layers demonstrated a statistically significant difference between the nasal and temporal sides for any decade of life.

There were statistically significant changes in the NRS of the NFL and ellipsoid layer with age (P<0.001, FIG. 7A). The NRS of the NFL decreased with increasing age and became significantly different from baseline (age group 10-19) in age group 30-39 on the nasal side (1168 vs 882 units; P<0.001) and in age group 70-79 on the temporal side (673 vs 483 units; P=0.02). The NRS of the ellipsoid layer also decreased with increasing age and became significantly different from baseline (age group 10-19) in age group 40-49 on both the nasal and temporal sides (FIG. 8). All other layers failed to demonstrate significant changes in NRS with age.

Figure 10:
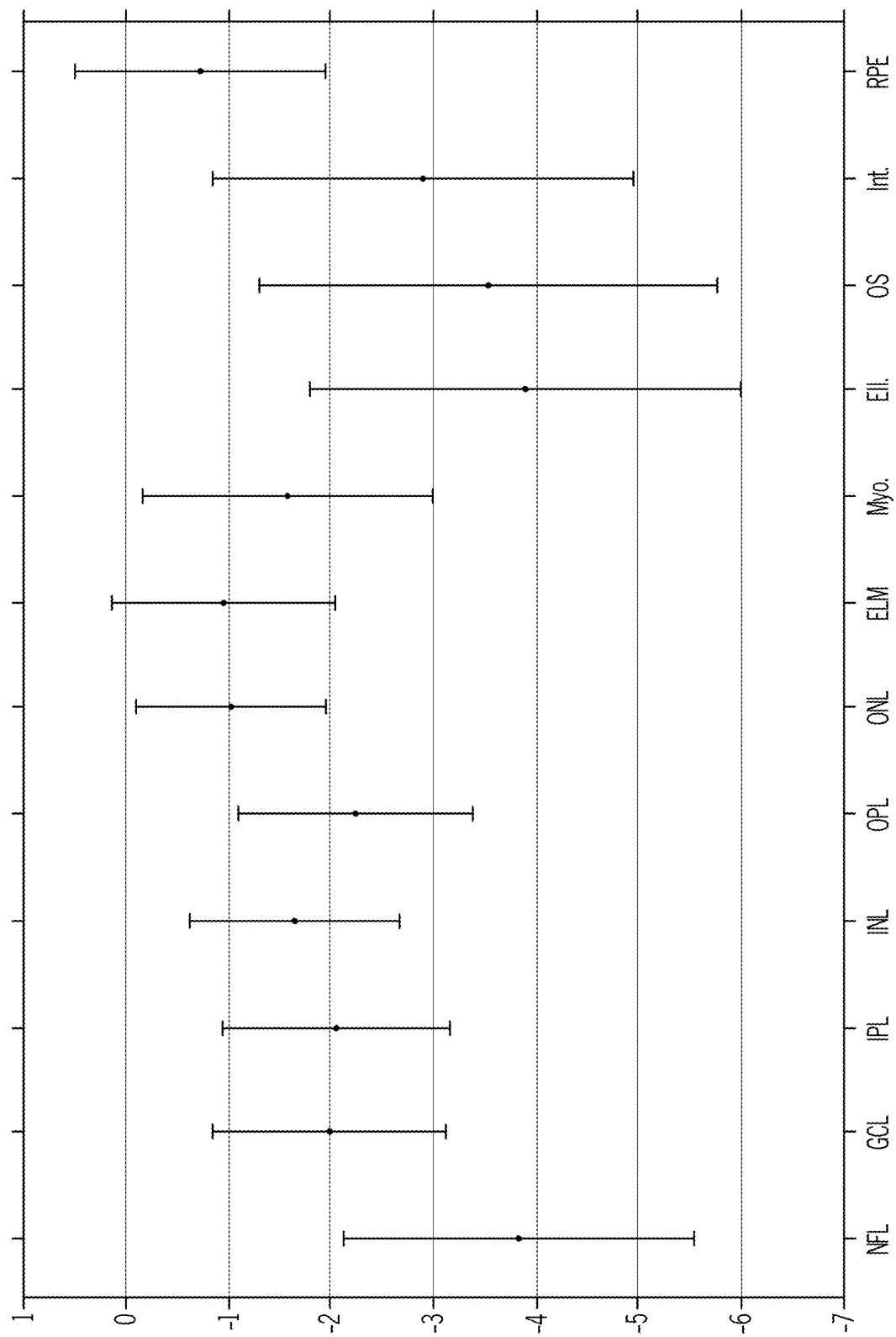
FIG. 10) graph showing the rate of change in NRS as a function of age for each segmented layer of the retina with 95% confidence intervals.

Overall, the normalized reflectivity varied significantly with age ($F_{1,4368}$=327; p<0.0001), gender ($F_{1,4368}$=5.11; p=0.024), and layer ($F_{11,4368}$=2330; p<0.0001), but not side of the fovea ($F_{1,4368}$=0.424; p=0.515). The slope, or year to year change in NRS, varied significantly by retinal layer ($F_{11,4368}$=14.77; p<0.0001) (FIG. 10). The interactions of side of the fovea with layer was statistically significant ($F_{11,4368}$=29.1; p<0.0001). No other terms in the model were significant. The gender effect, while statistically significant, amounted to only 1.4 NRS (male>female). NRS decreased with age overall (FIG. 8), with the greatest declines seen in the ellipsoid zone (−3.43 NRS·yr−1), and NFL (−3.50 NRS·yr−1). Normal aging had little to no effect on the RPE (−0.72 NRS·yr−1).

CONCLUSION

The visual function deterioration with aging has been the focus of multiple studies in the past. Standard full-field ERGs show a significant increase in implicit times and a decrease in the amplitudes of a- and b-waves with aging. A reduction in amplitude density of the central 108 diameter of vision in multifocal ERGs has also been demonstrated with normal aging. At the structural level, rods appear to be more affected by aging than do cones. It was previously shown that between the ages of 34 and 90 years, the number of cones in the macular area remains stable, while the density of rods decreases by 30% in the central retina. The number of ganglion cells in the fovea and peripheral retina also decreases during aging. The translation of the above changes that occur with normal aging into the morphological changes on OCT images has not been studied or objectively assessed.

The present results demonstrate that although no significant change in reflectivity was noted in the ganglion cell layer with aging, the reflectivity of the NFL decreased both in the temporal and nasal parts of the parafovea. This may in part be due to the differential rate of age-related loss between their axons. The orientation of the axons in the NFL, compared to the orientation of nuclei in the GCL, may also contribute to a differential loss of reflectivity between the layers. Additionally, it has been shown that the optic nerves of aging mice contain a significant number of necrotic axons in the process of being phagocytosed. The corresponding structural changes may influence the reflectivity of the NFL. This phenomenon might also be due to the characteristic of aging which display higher levels of cytoplasmic organelles.

The other retinal layer which showed significant changes with aging was the ellipsoid zone, which is the product of the high concentration of photoreceptor mitochondria in this region. The outer retina is exposed to sunlight and to a relatively high oxygen tension. The photoreceptor membranes are rich in polyunsaturated fatty acids, and the combination of these different elements results in a tissue that is especially prone to oxidative damage. Mitochondrial DNA (mtDNA) mutations progressively accumulate in photoreceptors with time, particularly in the foveal region. The accumulation of mtDNA mutations induces apoptosis and may play a role in what was observed as reduction of ellipsoid reflectivity with normal aging. Additionally, mitochondria undergo structural and functional alterations with aging that may contribute to either a change in the highly structured arrangement of mitochondria within the ellipsoid zone, in the local physiology, or both.

All other retinal layers failed to change significantly in reflectivity across the age groups examined. This may speak to the relative maintenance of retinal cell counts in the fovea. Considering the dense population of cones in the fovea and in accordance with histopathological findings of aging, no significant difference in ONL reflectivity with aging was observed. Interestingly, both the inner and outer plexiform layers did show a non-significant decrease in reflectivity with age. This may be consistent with the hypothesis generated from analysis of the NFL and GCL that layers consisting of axons may show reflectivity changes sooner than layers consisting of nuclei despite their obvious connectedness.

The accumulation of lipofuscin in the RPE is another major change that occurs during aging. However, the reflectivity of the RPE did not significantly change after the $3^{rd}$ decade of life. This may be explained by the fact that the primary OCT correlate within the RPE is the melanosome.

Example 4

This example shows the performance advantages of the inventive segmentation algorithm over a graph theory based approach exemplified by Gwet K L, *J. Math Stat Psychol.* (2008). The Gwet approach produces a mean boundary error of 284 micrometers, and only the RPE/choroid boundary was reliably detected, with mean error of 15.1 micrometers, standard deviation of 8.6 micrometers. The AC1 was very low; whereas the DSC mean was 30.3% (s.d. 0.358) in ONL-EZ (outer nuclear layer and inner segments of photoreceptors) and 40.7% (s.d. 0.194) in OPR-RPE (hyperreflective complex). The DSC mean was zero elsewhere.

Comparative segmentation results of embodiments of the invention versus Gwet for some selected data are demonstrated in Table 1, which summarizes a quantitative comparison of an inventive segmentation method and Gwet, both versus the ground truth, based on the three evaluation metrics for all subjects. Statistical analysis using paired t-test demonstrates a significant difference in terms of all three metrics of our method over Gwet, as confirmed by p-values <0:05 (see Table 1). This analysis clearly demonstrates the superiority of the inventive methods for the segmentation of the OCT scans.

TABLE 1

Comparative segmentation accuracy of the proposed segmentation technique and a known segmentation approach

| | Evaluation Metric | | |
|---|---|---|---|
| | DSC | AC1, % | AD, μm |
| Inventive+ | 0.763 ± 0.1598 | 73.2 ± 4.46 | 6.87 ± 2.78 |
| Gwett | 0.41 ± 0.263 | 2.25 ± 9.7 | 15.1 ± 8.6 |
| p-value | <0.0001 | <0.0001 | <0.00395 |

After excluding low quality and tilted scans, reflectivity was measured in the right eye of 138 women and 62 men, between 10 and 76 years of age. The female subgroup was slightly older on average at 43.7 years compared to 37.6 years for the male subgroup (t106=1.91; p=0.059).

Example 5

The following example illustrates application of an embodiment of the segmentation algorithm providing automated quantification of SD-OCT images to permit detection of occult/subtle early changes in the Diabetic Retina Diabetes inevitably results in diabetic retinopathy (DR) with time. SD-OCT imaging is used to assess diabetic changes in the retina, however these changes are apparent only late in the disease, when the retinal anatomy is already compromised. An embodiment is exemplified directed to an automated algorithm to detect occult retinal changes on SD-OCT images prior to the development of obvious anatomical or clinical changes.

Methods: Spectral domain OCT scans (Zeiss Cirrus HD-OCT 5000) were obtained from 16 diabetic subjects aged 53-76 years without clinical evidence of DR. 16 healthy subjects, matched for sex and age were used as controls. Subjects with high myopia (≤−6.00 diopters) or tilted OCT scans were excluded. Twelve distinct layers were first segmented using an embodiment of the disclosed automated algorithm that combines shape, intensity, and spatial information. A novel normalized reflectivity scale (NRS) ranging from 0 units (vitreous) to 1000 units (retinal pigment epithelium [RPE]) was then applied to calculate the reflectivity for each segmented layer from the raw data. Tortuosity of retinal layers was quantified using the mean absolute curvature κ of the boundary between adjacent layers.

Figure 11:
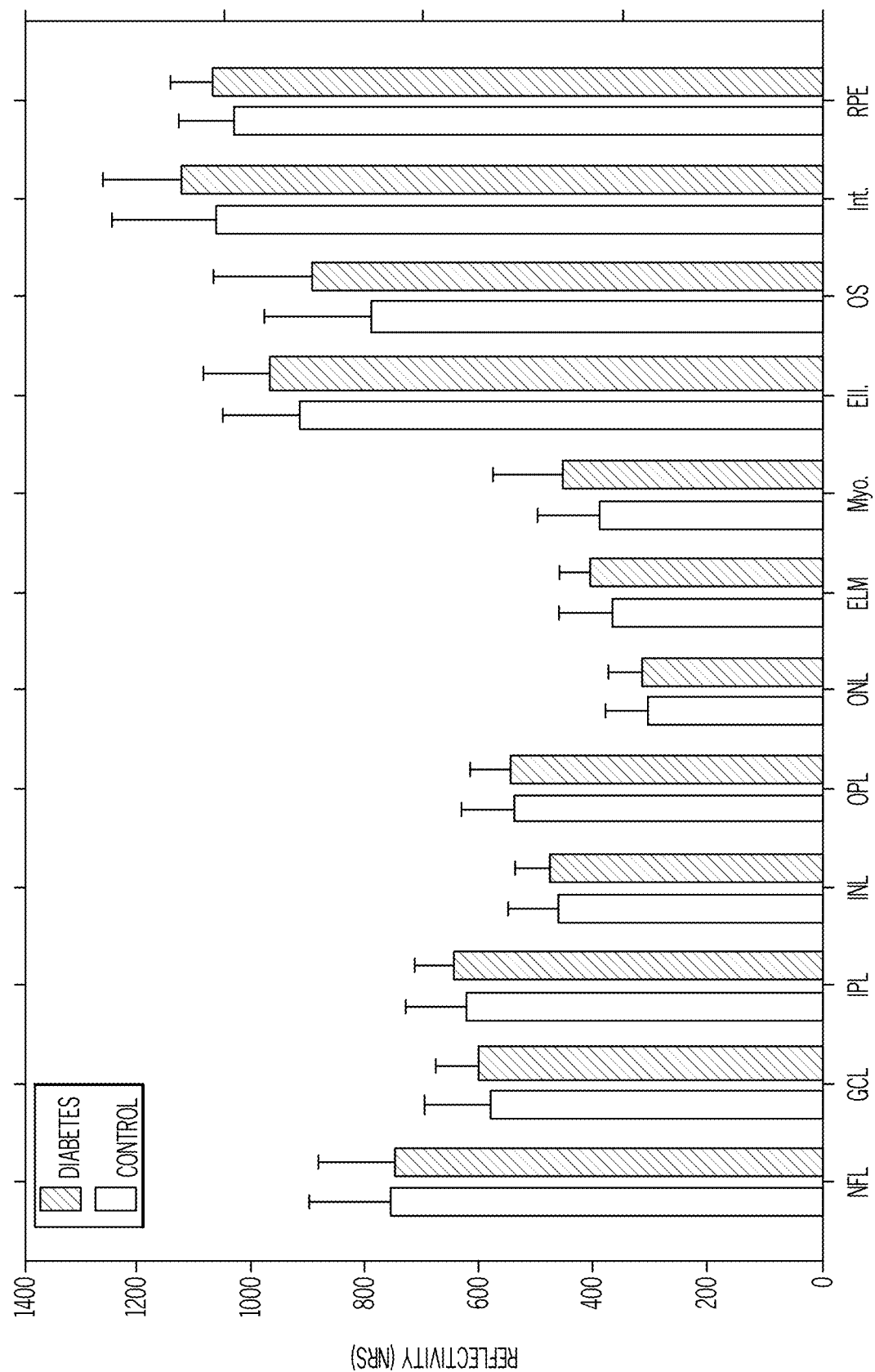
FIG. 11) depicts a bar graph comparing NRS in normal and diabetic eyes for all 12 retinal layers, showing mean and standard deviation in NRS. Although there were no significant observable differences in the layers between diabetics and controls, the NRS scaling in accordance with embodiments of the invention revealed that NRS varies significantly by diagnosis ($F_{1,658}=24.18$; $p<0.0001$) and retinal layer ($F_{11,658}=457.3$; $p<0.0001$)
Figure 12:
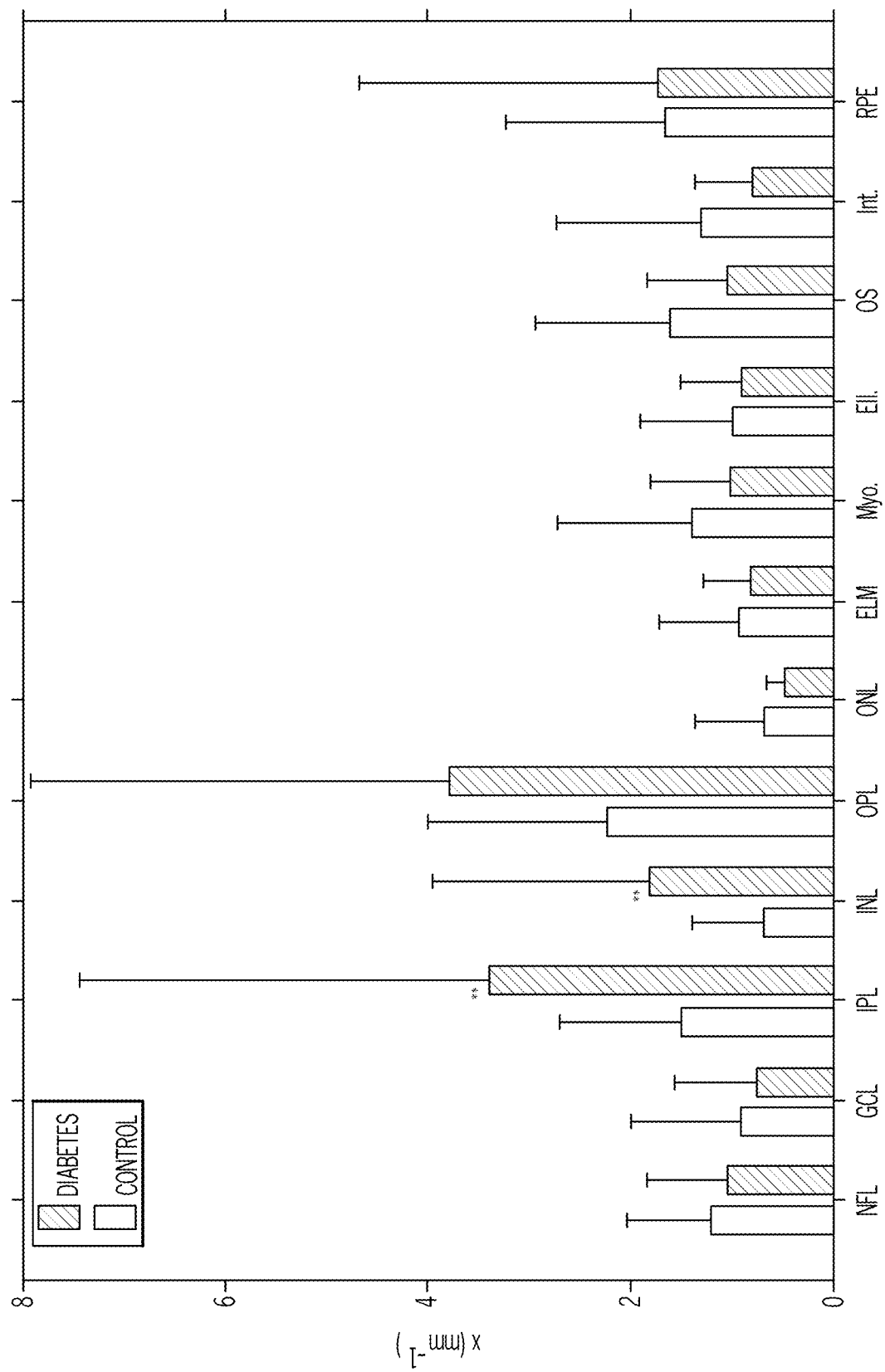
FIG. 12) depicts a bar graph comparing the mean and standard deviation of tortuosity per layer and diagnosis. Tortuosity of a layer is the mean absolute curvature of the boundary between it and the next layer anterior, or the choroid in the case of RPE. Control and diabetic subjects demonstrated significant differences (Benjamini-Hochberg corrected $p<0.05$).

Results: As set forth in FIG. 11, although there was no observable overt clinical difference between the normal and diabetic eyes, the normalized reflectivity varied significantly by diagnosis ($F_{1,658}$=24.18; p<0.0001) and retinal layer ($F_{11,658}$=457.3; p<0.0001). Reflectivity per layer differed by side of the fovea ($F_{11,658}$=6.13; p<0.0001). Reflectivity in diabetic subjects in all layers was in average 35.1 NRS greater than in their matched controls (FIG. 11). Curvature varied significantly by layer ($F_{11,658}$=11.9; p<0.0001) and side ($F_{1,658}$=6.63; p=0.010). Post hoc testing revealed significant differences in the IPL and INL where κ averaged 1.91 mm$^{-1}$ and 1.12 mm$^{-1}$ greater, respectively, in diabetes compared to control (FIG. 12).

Conclusion: An automated image analysis algorithm allows the identification of subtle changes in diabetic retinas that occur prior to the disruption of normal anatomy. Detection of such changes carries the promise of early diagnosis of DR in diabetics.

Example 6

The following is an example of computer programming executable to carry out embodiments of the invention relating to segmenting and quantifying a retinal characteristic (specifically reflectivity).

The invention claimed is:

1. A retinal OCT segmentation algorithm for segmenting a test retinal OCT image into 13 retinal regions, the algorithm comprising:
   (a) providing a probabilistic shape and intensity model derived from a plurality of OCT images generated from control subjects and segmented into 13 retinal regions;
   (b) aligning the test OCT image with the probabilistic shape and intensity model according to retinal region shape;
   (c) comparing pixels of the aligned test OCT image with the corresponding pixels in the control model by intensity, establishing a probable regional fit, and refining regional margins by estimating marginal density distribution with a linear combination a linear combination of discrete Gaussians (LCDG) to generate an initial regional segmentation map of the test OCT image comprising defined retinal regions; and
   (d) fitting the initial segmentation map with a statistical model that accounts for spatial information to achieve a final segmentation map comprising 13 retinal regions.

2. The method according to claim 1, wherein the alignment of step (b) comprises (i) constructing a wavelet decomposition of the test image, (ii) detecting at least three regional boundaries, (iii) identifying the foveal pit by reference to the detected boundaries, (iv) placing fiduciary points on each detected boundary at locations equidistant from the foveal pit, and (v) aligning the test image to the model image by aligning the fiduciary points.

3. The method according to claim 1, wherein the statistical model that accounts for spatial information is a Markov-Gibbs Random Field model.

4. The method according to claim 1, wherein the comparing of step (c) comprises (i) constructing a closed set around each aligned test image pixel, (ii) identifying within the set a corresponding model pixel having intensity nearest the image pixel, and (iii) determining a probability of the aligned test pixel being in one of the 13 retinal regions of the model.

5. The method according to claim 1, wherein the 13 retinal regions comprise the vitreous, nerve fiber layer (NFL), ganglion cell layer (GC), inner plexiform layer (IPL), internal limiting membrane (ILM), inner nuclear layer (INL), outer plexiform layer (OPL), outer nuclear layer (ONL), external limiting membrane (ELM), inner segments (IS), inner/outer segment junction (I/OS), outer segments of the photoreceptors (OSP), and retinal pigment epithelium (RPE).

6. The method according to claim 1 wherein the method is executed automatically by a computer.

7. The method according to claim 1, wherein the control subjects of step (a) are selected from one of: normal subjects, subjects suffering from a specific retinal pathology, or subjects of a specific demographic profile, said profile comprising one or more of age, gender, race, geographic residence and ethnicity.

8. A method of quantifying a retinal characteristic from retinal OCT image data, the method comprising:
 (a) obtaining a retinal spectral domain-OCT image from a subject;
 (b) segmenting the OCT image into retinal regions according to a retinal OCT segmentation algorithm, said regions comprising the vitreous and the retinal pigment epithelium (RPE), and one or more additional regions;
 (c) calculating a mean raw characteristic value within each region;
 (d) assigning the vitreous region mean raw characteristic value equal to zero normalized characteristic units, and assigning the RPE region mean raw characteristic level equal to X normalized characteristic units;
 (e) converting the calculated mean raw characteristic values for each of the one or more additional regions based on an offset and uniform scale to yield a control normalized characteristic unit scale from 0 to X; and
 (f) quantifying the characteristic according to the normalized characteristic unit scale.

9. The method according to claim 8, wherein a normalized characteristic unit scale is calculated for at least two areas within each region, said areas selected from left nasal, left temporal, right nasal, right temporal, "left" and "right" being relative to the fovea.

10. The method according to claim 9, wherein the retinal characteristic is reflectivity, a characteristic normalized value is a reflectivity unit (RU), X=1000, and the normalized characteristic unit scale is a normalized reflectivity scale.

11. A method of diagnosing an ocular pathology in a subject, the method comprising:
 (a) obtaining at least one OCT retinal image of the subject;
 (b) quantifying reflectivity in at least one diagnostically relevant retinal region of the subject OCT image according to the method of claim 10;
 (c) comparing the quantified reflectivity of the retinal region of the subject OCT image to a control quantified reflectivity derived from either normal control OCT images or pathology-specific control OCT images, to determine a difference if the control reflectivity is derived from normal control subjects, and a fit if the control reflectivity is derived from pathology-specific subjects;
 (d) statistically assessing the difference or fit; and
 (e) diagnosing an ocular pathology if the difference or fit is statistically significant.

12. The method of claim 11, further comprising the steps of:
 (f) calculating thickness or curvature of at least one diagnostically relevant retinal region of the subject OCT image;
 (g) calculating a mean thickness or curvature of the at least one diagnostically relevant retinal regions of the control OCT images;
 (h) comparing the calculation (f) to calculation (g); and
 (i) determining a statistically significant difference or fit of the subject OCT image retinal region thickness and/or curvature over the control OCT image retinal region thickness and/or curvature, wherein a statistically significant difference from a normal control or a statistically significant fit to a pathology-specific control indicates a diagnosis of ocular pathology.

13. The method of diagnosing an ocular pathology according to claim 12, wherein the ocular pathology is selected from age-related macular degeneration (AMD), choroideremia, Stargardt disease, Usher syndrome, diabetic retinopathy, macular hole/pucker, retinoblastoma, retinal detachment, river blindness/onchocerciasis, and retinitis pigmentosa.

14. The method of diagnosing an ocular pathology according to claim 13, wherein the subject is at risk for developing diabetic retinopathy but does not manifest clinical symptoms of diabetic retinopathy, wherein a diagnosis of diabetic retinopathy is indicated where: (i) subject OCT image normalized reflectivity values are greater than the normal control OCT image normalized reflectivity values for a majority of retinal regions, and/or (ii) subject normalized reflectivity values within at least one retinal region differ significantly between left and right regional areas, and/or (iii) curvature and thickness of subject OCT segmented retinal regions vary by retinal region and by left and right regional area for at least two retinal regions.

15. The method according to claim 14, wherein the at least two retinal regions of (iii) comprise inner plexiform layer (IPL) and inner nuclear layer (INL).

16. The method of diagnosing an ocular pathology according to claim 13, wherein the subject is at risk for developing glaucoma, wherein a diagnosis of glaucoma is indicated where: (i) subject OCT image normalized reflectivity values in the NFL retinal region are greater than normal control OCT image normalized reflectivity values in the NFL retinal region, and (ii) subject OCT image thickness of the NFL retinal region is less than normal control OCT image thickness of the NFL retinal region.

17. The method according to claim 11, wherein the control OCT images are derived from age-matched subjects.

18. A method of monitoring age-related retinal change in a subject, the method comprising:
 obtaining at least two OCT retinal images of the subject across a longitudinal time frame; quantifying reflectivity of each retinal OCT image according to the method of claim 10; comparing the quantified reflectivity of the at least two OCT retinal images; and monitoring age-related retinal change in the test subject, based on the comparison.

19. A method of managing an age-related chorioretinal disease in a subject comprising:
(a) obtaining at least a first OCT retinal image and a second OCT retinal image of the subject across a longitudinal time frame;
(b) quantifying reflectivity of each OCT retinal image according to the method of claim 10;
(c) comparing the quantified reflectivity of the first OCT retinal image with the quantified reflectivity of the second OCT retinal image; and
(d) managing the age-related chorioretinal disease based on the comparison.

20. The method according to claim 19, wherein the age-related chorioretinal disease is associated with neovascular age-related macular degeneration.

21. A method of monitoring retinal response to treatment of a subject with a pharmaceutical agent, the method comprising:
(a) obtaining a retinal OCT image of at least one retina of the subject prior to initiation of treatment with the pharmaceutical agent;
(b) obtaining a retinal OCT image of the at least one retina of the subject after initiation of treatment with the pharmaceutical agent;
(c) quantifying reflectivity of each OCT retinal image according to the method of claim 10;
(d) comparing the quantified reflectivities of step (c) and determining statistically significant differences, and
(e) determining a retinal response to treatment where a statistically significant difference is observed.

22. The method according to claim 21, wherein the retinal response comprises macular remodeling.

23. The method according to claim 21, wherein the subject suffers from glaucoma and the retinal response is cessation or reversal of nerve fiber layer (NFL) atrophy.

24. The method according to claim 8, wherein the segmentation algorithm comprises:
(a) providing a probabilistic shape and intensity model derived from a plurality of OCT images generated from control subjects and segmented into a plurality of retinal regions;
(b) aligning the test OCT image with the probabilistic shape and intensity model according to retinal region shape;
(c) comparing pixels of the aligned test OCT image with the corresponding pixels in the control model, establishing a probable regional fit, and refining regional margins to generate an initial regional segmentation map of the test OCT image comprising defined retinal regions; and
(d) fitting the initial segmentation map with a statistical model that accounts for spatial information to achieve a final segmentation map comprising the plurality of retinal regions.

25. A non-transitory computer readable media storing computer-executable instructions, which when executed by a computer, cause the computer to carry out a method comprising:
(a) receiving a test OCT image of a retina;
(b) segmenting the test OCT image into 13 retinal regions based on a retinal OCT image model incorporating shape, intensity and spatial information derived from a control group of OCT images, wherein the 13 retinal regions comprise: vitreous, nerve fiber layer (NFL), ganglion cell layer (GC), inner plexiform layer (IPL), internal limiting membrane (ILM), inner nuclear layer (INL), outer plexiform layer (OPL), outer nuclear layer (ONL), external limiting membrane (ELM), inner segments (IS), inner/outer segment junction (I/OS), outer segments of the photoreceptors (OSP), and retinal pigment epithelium (RPE), further wherein reflectivity of each retinal region is quantified with a reflectivity unit value according to a normalized reflectivity scale;
(c) deriving a normalized reflectivity scale for the test OCT image and assigning a reflective unit value to each retinal region based on the normalized reflectivity scale;
(d) comparing the assigned reflective unit values of each retinal region of the test OCT image to the model reflective unit values for the same retinal regions; and
(e) diagnosing a retinal pathology by correlating the comparison result of (d) with a database of retinal pathologies associated with normalized reflectivity scales specific to each retinal pathology.

* * * * *